(12) United States Patent
Zhang et al.

(10) Patent No.: US 12,038,420 B2
(45) Date of Patent: Jul. 16, 2024

(54) EARLY WARNING METHOD BEFORE OCCURRENCE OF AFLATOXIN CONTAMINATION

(71) Applicant: OIL CROPS RESEARCH INSTITUTE, CHINESE ACADEMY OF AGRICULTURAL SCIENCES, Hubei (CN)

(72) Inventors: Qi Zhang, Hubei (CN); Peiwu Li, Hubei (CN); Huali Xie, Hubei (CN); Xiupin Wang, Hubei (CN); Xiaofeng Yue, Hubei (CN); Wen Zhang, Hubei (CN)

(73) Assignee: OIL CROPS RESEARCH INSTITUTE, CHINESE ACADEMY OF AGRICULTURAL SCIENCES, Hubei (CN)

( * ) Notice: Subject to any disclaimer, the term of this patent is extended or adjusted under 35 U.S.C. 154(b) by 335 days.

(21) Appl. No.: 17/502,062

(22) Filed: Oct. 15, 2021

(65) Prior Publication Data

US 2022/0120722 A1     Apr. 21, 2022

(30) Foreign Application Priority Data

Oct. 15, 2020   (CN) .......................... 202011106656.3

(51) Int. Cl.
*G06F 11/30* (2006.01)
*G01N 30/72* (2006.01)
*G01N 30/86* (2006.01)

(52) U.S. Cl.
CPC ..... *G01N 30/8675* (2013.01); *G01N 30/7233* (2013.01); *G01N 30/8631* (2013.01); *G01N 30/8693* (2013.01)

(58) Field of Classification Search
CPC ....................................................... G01N 3/08
See application file for complete search history.

(56) References Cited

U.S. PATENT DOCUMENTS 5,292,661 A  *  3/1994  Cole  ...................... C12N 1/145
                                                        435/267

FOREIGN PATENT DOCUMENTS

CN            1696696 A  *  11/2005
WO       WO-9726364 A1  *   7/1997    ......... C12N 15/8242

* cited by examiner

*Primary Examiner* — Phuong Huynh
(74) *Attorney, Agent, or Firm* — JCIP GLOBAL INC.

(57) ABSTRACT

The present invention relates to an early warning method before the occurrence of aflatoxin contamination. The steps are as follows: extracting toxins from the sample to obtain a sample extract, and subjecting the sample extract to detection and analysis by liquid chromatography-high resolution mass spectrometer, performing qualitative analysis based on the mass spectrometry information to obtain qualitative results, performing quantitative analysis based on a standard curve of the chromatographic peak area of each warning molecule/the peak area of the internal standard-warning molecule concentration to obtain quantitative results of these warning molecules, wherein a risk of aflatoxin contamination of the sample is assessed to obtain a classification prediction model, inputting the quantitative results of the warning molecules for a toxigenic strain of *Aspergillus flavus*, and outputting a risk assessment result based on the classification prediction model, thereby achieving the early warning before aflatoxin contamination occurs.

9 Claims, 17 Drawing Sheets

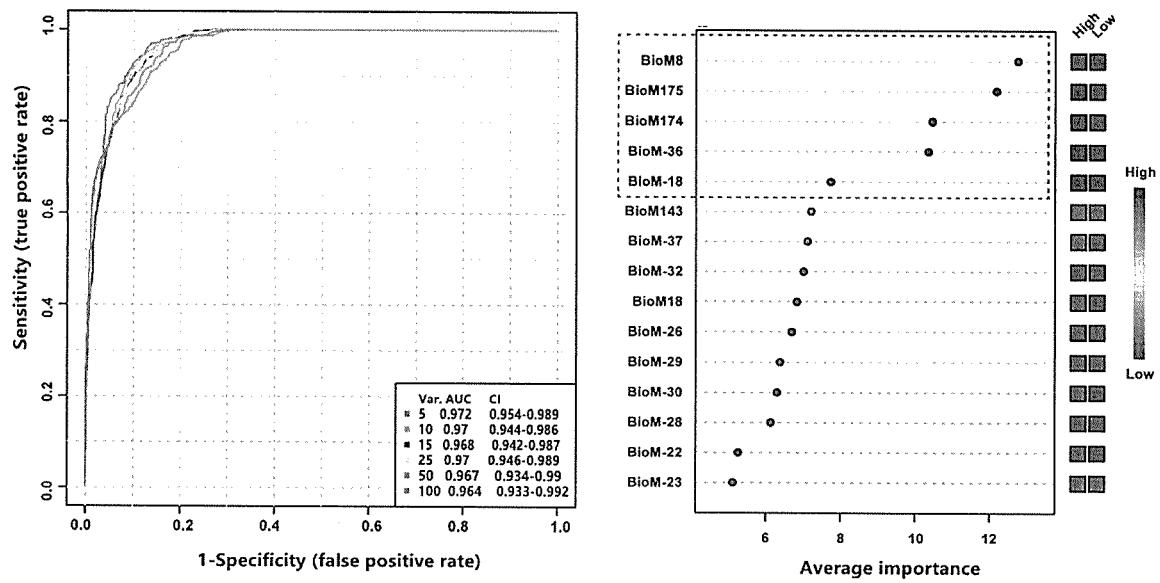
Fig.5(a)
Fig.5(b)
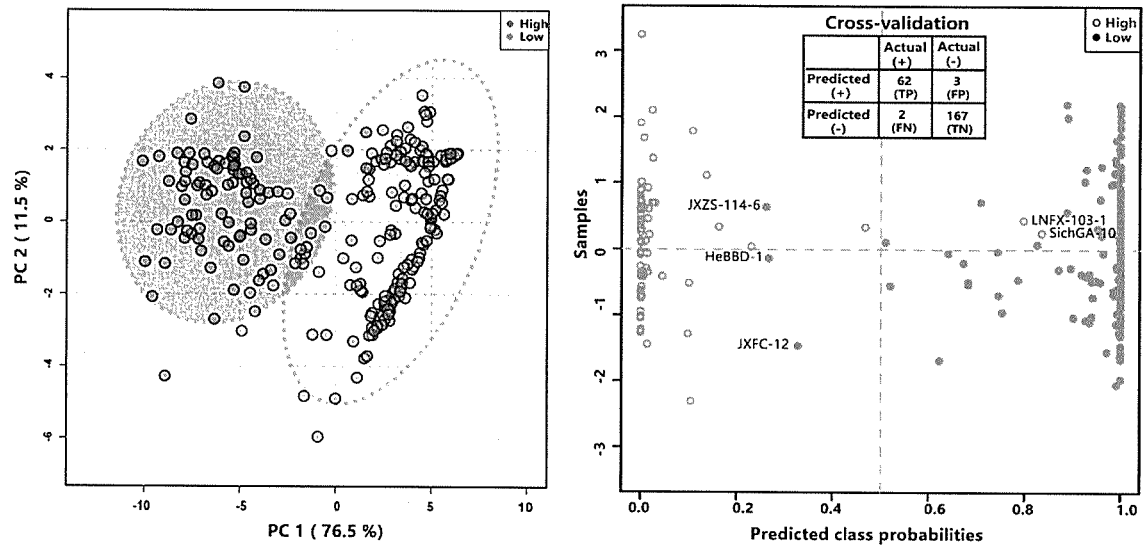
Fig.5(c)
Fig.5(d)

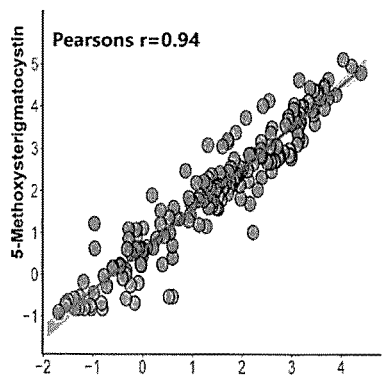
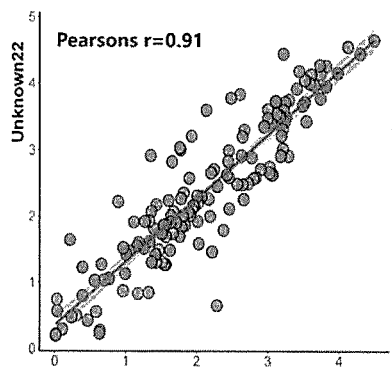
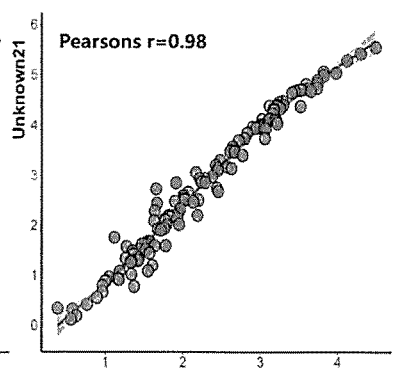
Fig.6(a)  Fig.6(b)  Fig.6(c)
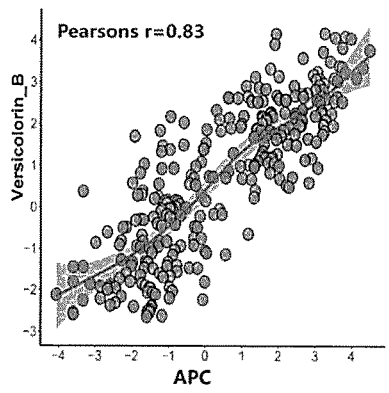
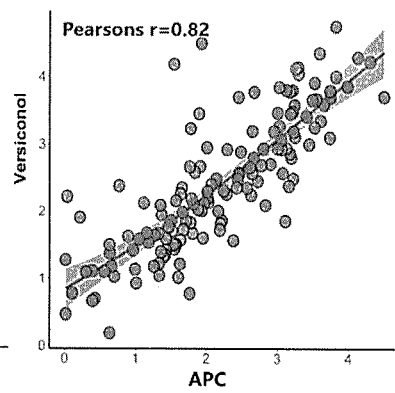
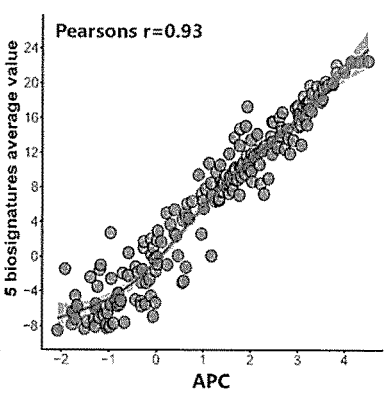
Fig.6(d)  Fig.6(e)  Fig.6(f)
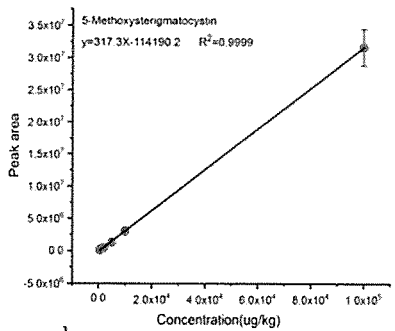
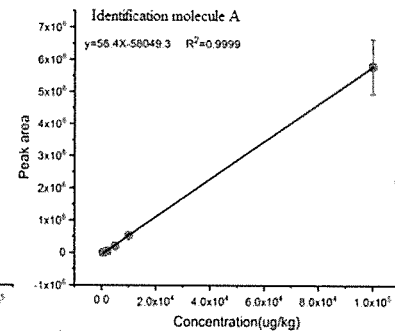
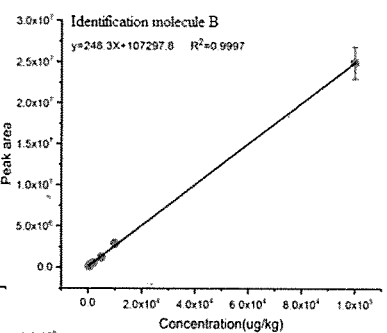
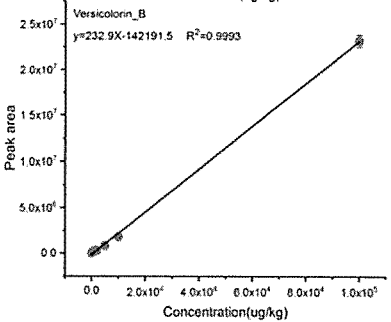
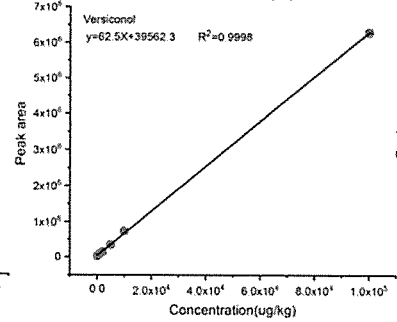
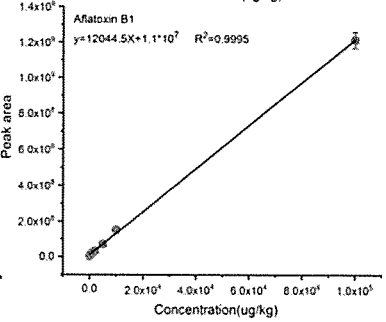
Fig.7

EARLY WARNING METHOD BEFORE OCCURRENCE OF AFLATOXIN CONTAMINATION

CROSS-REFERENCE TO RELATED APPLICATION

This application claims the priority benefit of China application serial no. 202011106656.3, filed on Oct. 15, 2020. The entirety of the above-mentioned patent application is hereby incorporated by reference herein and made a part of this specification.

BACKGROUND

Technical Field

The present disclosure relates to an early warning method before the occurrence of aflatoxin contamination, and belongs to the field of analysis and detection.

Description of Related Art

Mycotoxins are secondary metabolites generated from filamentous fungi, and may, in an entire industrial chain, contaminate peanuts, corn, cotton, nuts and other crops. They have a high incidence worldwide, causing huge economic losses due to mycotoxin contamination of 25% of crops each year in the world, while seriously endangering people's lives and health. For example, they have carcinogenic, immunosuppressive, hepatotoxic, nephrotoxic and neurotoxic properties, and the like. Aflatoxin is mainly derived from *Aspergillus flavus*, and is considered to be one of the ten most horrible fungi in the world. This fungus is widely distributed in the world, including China, and is a major causative factor of regional liver cancer in China. Currently, many countries have established a strict aflatoxin limit standard, so as to ensure the quality and safety of agricultural products and avoid the trade barrier from aflatoxin. It is obvious that the development of an early aflatoxin warning method becomes urgent.

The contamination risk of aflatoxin is mainly classified into contamination by toxigenic *Aspergillus flavus* and contamination by aflatoxin.

In the present disclosure, in order to realize the risk warning of aflatoxin contamination, two strategies are provided: (1) a toxigenic *Aspergillus flavus* bio-warning molecule is developed to early identify the toxigenicity of *Aspergillus flavus* in peanuts or soil so as to early warn aflatoxin contamination; and (2) the severity of aflatoxin contamination is predicted by dynamically monitoring the toxigenicity-related warning molecules. It is well known that fungi have evolved thousands of secondary metabolites as a chemical weapon or armor to occupy favorable ecological niches and protect their food from competitors. Theoretically, these diversities pave the way for screening of a bio-warning molecule for toxigenic *Aspergillus flavus* at the subspecies level in this study. Herein, we provide that the metabolic diversity properties of the *Aspergillus flavus* population may be systematically investigated in combination with machine learning techniques to screen warning molecules that may effectively distinguish high- and low-toxigenicity strains, and to predict the severity of aflatoxin contamination in agricultural products based on the dynamics of the warning molecules.

SUMMARY

The technical problem to be solved by the present disclosure is to provide an early warning method before the occurrence of aflatoxin contamination based on warning molecules for an aflatoxigenic strain in view of the lack of early warning before the occurrence of aflatoxin contamination.

In order to solve the above technical problem, the technical solution adopted by the present disclosure is as follows.

An early warning method before the occurrence of aflatoxin contamination includes the following steps:

weighing a quantitative sample, extracting toxins from the sample to obtain a sample extract, and subjecting the sample extract to detection and analysis by liquid chromatography-high resolution mass spectrometer, collecting mass spectrometry information, and performing qualitative analysis based on the mass spectrometry information to obtain qualitative results of versiconol (VOH), versicolorin B (Ver B), 5-methoxysterigmatocystin (5-MST), a warning molecule A and a warning molecule B, and according to its corresponding chromatographic peak area in combination with an internal standard, performing quantitative analysis based on a standard curve of the chromatographic peak area of each warning molecule/the peak area of the internal standard-warning molecule concentration to obtain quantitative results of these warning molecules.

The qualitative analysis shown is performed by determining the primary and secondary mass spectrometry information of the warning molecules in the sample, comparing the accurate mass number of the primary mass spectrometry of each warning molecule with the theoretical value thereof to obtain a deviation of the mass spectrometry being within 5 ppm, and then comparing main characteristic ion peaks of the secondary mass spectrometry in combination with the secondary mass spectrometry information.

The primary mass spectrometry peak information of each warning molecule is as follows:

| | | Accurate mass number | |
|---|---|---|---|
| Warning molecule | Ion mode | Theoretical value | Measured value |
| 5-Methoxy-sterigmatocystin $C_{19}H_{14}O_7$ | $[M + H]^+$ | 355.08122 | 355.08068 |
| Warning molecule A $C_{43}H_{18}O_7$ | $[M + H]^+$ | 647.11147 | 647.11469 |
| Warning molecule B $C_{19}H_{14}O_7$ | $[M + Na]^+$ | 377.06289 | 377.06238 |
| Versicolorin_B $C_{18}H_{12}O_7$ | $[M - H]^-$ | 339.05102 | 339.05096 |
| Versiconol $C_{18}H_{16}O_8$ | $[M - H]^-$ | 359.07724 | 359.07733 |

The main characteristic peaks in the secondary mass spectrum of the warning molecule A include 335.05045 Da, 320.02655 Da, and 291.0243 Da.

The main characteristic peaks in the secondary mass spectrum of the warning molecule B include 362.03836 Da, 333.0355 Da, and 319.0204 Da.

The mass spectra of each warning molecule are shown in FIG. 11(*a*)-(*e*).

A risk of aflatoxin contamination of the sample is assessed by performing modeling with a chemometrics method by using the content of the warning molecule A, or the content of the warning molecule B, or the content of one or more of the warning molecule A and the warning molecule B and one or more of versiconol (VOH), versicolorin B (Ver B) and 5-methoxysterigmatocystin (5-MST) as a variable to obtain a classification prediction model, inputting the quantitative results of the warning molecules for a toxigenic strain of

*Aspergillus flavus*, and outputting a risk assessment result based on the classification prediction model.

According to the above solution, the chemometrics method is a multivariate statistical analysis method such as hierarchical cluster analysis, least partial square orthogonal projection, and random forest.

According to the above solution, after the sample is cultured for 3-4 days, the sample is taken for detection of warning molecules for toxigenic *Aspergillus flavus*, and the quantitative values of the warning molecules such as versiconol (VOH), versicolorin B (Ver B), 5-methoxysterigmatocystin (5-MST), the warning molecule A and the warning molecule B are input to the classification prediction model to predict aflatoxin risk.

According to the above solution, the above method further includes screening a suspected sample, pre-treating the screened suspected sample, detecting the warning molecules for toxigenic *Aspergillus*, and outputting risk assessment results based on the classification prediction model to perform risk assessment for the risk of aflatoxin contamination of the sample, specifically: detecting the aflatoxin content of the sample; subjecting a sample in which aflatoxin is not detected or the aflatoxin content does not exceed the standard to an accelerated microbial metabolism culture experiment (that is, added to a sterile culture dish containing a mold medium, and placed in a constant temperature incubator to be incubated for 3-4 days), wherein *Aspergillus* will grow in the suspected contaminated sample; quenching the suspected sample by liquid nitrogen and grinding for later use; and detecting the aflatoxin content of the sample, wherein the sample with the aflatoxin content higher than a national limit standard is directly identified as a high-risk sample, that is, the suspected sample.

According to the above solution, the sample is an agricultural product or food, including peanuts, and so on.

According to the above solution, extracting the warning molecules for the toxigenic strain of *Aspergillus flavus* includes: performing first extraction by using a solution with a volume ratio of methanol to acetonitrile to water being 2-4:2-4:0-1, and then performing second extraction by using another extraction solution with a volume ratio of methanol to dichloromethane to ethyl acetate being 1-3:1-2:1-2 to extract the warning molecules for the toxigenic strain of *Aspergillus flavus*, and then centrifugating at a high speed to obtain the sample extract.

According to the above solution, analyzing the sample includes: performing analysis of the sample by liquid chromatography-high resolution mass spectrometer, during analysis by the liquid chromatography-high resolution mass spectrometer, a chromatographic column is a $C_{18}$ reverse chromatographic column, and an acquisition mode during mass spectrographic analysis is is divided into a positive ion mode and a negative ion mode which are operated separately, the acquisition mode is a data-dependent acquisition mode, and the primary mass spectrometry data and secondary fragment ion data are acquired simultaneously to perform qualitative and quantitative analysis, thereby obtaining the analysis results of the warning molecules.

According to the above solution, the detection and analysis by liquid chromatography-high resolution mass spectrometer contains an internal standard substance, and the internal standard is camphoric acid (a negative ion mode) and 2-chlorophenylalanine (a positive ion mode).

The standard curve of the chromatographic peak area of each early warning molecule/the peak area of the internal standard-early warning molecule concentration is as follows:

| warning molecule | regression equation |
| --- | --- |
| 5-Methoxysterigmatocystin | Y = 317.3X − 114190.2 |
| Warning molecule A | Y = 58.4X − 58049.3 |
| Warning molecule B | Y = 248.3X + 107297.8 |
| Versicolorin_B | Y = 232.9X − 142191.5 |
| Versiconol | Y = 62.5X + 39562.3 | wherein: X is the concentration of the warning molecule and Y is the chromatographic peak area/the peak area of the internal standard.

According to the above solution, the main characteristic peaks of secondary mass spectrogram for the warning molecule 5-methoxysterigmatocystin (5-MST) include 350.0809 Da, 340.0571 Da, 322.04675 Da, 311.05469 Da and 285.0098 Da.

The main characteristic peaks of secondary mass spectrogram for the warning molecule versiconol (VOH) include 329.06546 Da, 341.09506 Da, and 359.07596 Da.

The main characteristic peaks of secondary mass spectrogram for the warning molecule versicolorin B (Ver B) include: 311.0542 Da, 311.0187 Da, and 283.0238 Da.

According to the present disclosure, a machine learning algorithm, such as least partial square orthogonal projection, and random forest, is used to train a training set containing 334 samples so as to screen highly stable warning molecules for middle- or high-toxigenic strains. Preferably, the screened top 5 highly-stable identification warning molecules with the largest difference between high-toxigenicity strains and the low-toxigenicity strains have the best recognition effect on the classification model. The 5 warning molecules are 5-methoxysterigmatocystin, the warning molecule A (an identification molecule A), the warning molecule B (an identification molecule B), versiconol, and versicolorin_B. The remaining 234 samples are used as an independent validation set to validate the warning molecules by using the machine learning algorithm such as least partial square orthogonal projection and random forest. The validation results show that the top 5 warning molecules screened by the validation set have the same selection results as those of the training set, respectively being 5-methoxysterigmatocystin, the warning molecule A, the warning molecule B, versiconol, and versicolorin_B. As can be seen in FIG. 4(*a*), the combination of the 5 warning molecules makes the random forest model have the best classification and discrimination effect.

The screening of the warning molecule for toxigenic strains of aflatoxin described above specifically includes: the collected 568 samples are firstly divided into a training set of 334 samples, and an independent validation set of 234 samples. The training set containing 334 samples is trained by using a machine learning algorithm such as least partial square orthogonal projection and random forest, to screen highly stable warning molecules for middle- to high-toxigenic isolates, for example, BioM174 (a warning molecule A), BioM8 (5-Methoxysterigmatocystin), BioM175 (a warning molecule B), BioM-18 (Versiconol), and BioM-36 (Versicolorin_B), as shown in FIG. 4(*c*), wherein the molecular formula, accurate mass number, and other information of these molecules are shown in Table 1. The remaining 258 samples are then used as the independent validation set to validate the warning molecules. The validation result shows that the 5 warning molecules are also screened in the independent validation set and ranked in the top 5 (as shown in FIG. 5(*a*)-(*d*)). Further, the model constructed by the five warning molecules has the best prediction accuracy (as shown in FIG. 5(d)). Therefore, these warning molecules are selected to construct warning molecules for the toxigenic Aspergillus flavus strains, or the combination thereof, for the assessment of aflatoxin contamination.

TABLE 1

LC-HRMS information of aflatoxin B1 and biological warning molecules

| warning molecule and molecular formula | Ion mode | Accurate mass number theoretical value | Accurate mass number measured value | mass deviation (ppm) |
|---|---|---|---|---|
| Aflatoxin $B_1$ $C_{17}H_{12}O_6$ | $[M + H]^+$ | 313.07066 | 313.07012 | 1.73 |
| 5-Methoxy-sterigmatocystin $C_{19}H_{14}O_7$ | $[M + H]^+$ | 355.08122 | 355.08068 | 1.52 |
| molecular formula A | $[M + H]^+$ | 647.11147 | 647.11469 | 4.97 |
| molecular formula B $C_{19}H_{14}O_7$ | $[M + Na]^+$ | 377.06289 | 377.06238 | 1.35 |
| Versicolorin_B $C_{18}H_{12}O_7$ | $[M - H]^-$ | 339.05102 | 339.05096 | 0.17 |
| Versiconol $C_{18}H_{16}O_8$ | $[M - H]^-$ | 359.07724 | 359.07733 | 0.25 |

The beneficial effects of the present disclosure are.
1. According to the present disclosure, the metabolic diversity of the Aspergillus flavus population in China is systematically evaluated for the first time, and an advanced machine learning data analysis method is used to screen warning molecules for toxigenic Aspergillus flavus for the first time. An accurate warning molecule is provided for the identification of toxigenic fungi at the subspecies level, and an original warning molecule is provided for the early warning of mycotoxins. Meanwhile, the strategies of this study can draw inferences about other cases from one instance, and can be extended to all other microbial subspecies, providing a methodological reference for accurate identification and classification. A new way is provided to solve the problem that there is no warning molecule for early warning to monitor in the field of food quality and safety research.
2. The population metabolomics screening of warning molecules used in the present disclosure provides an example for early warning of mycotoxin contamination.
3. According to the present disclosure, a machine learning method is further used to screen the warning molecules to study the difference of different machine learning algorithms, and a combination of robust warning molecules is obtained by comparing the stability of different screening results so that the classification model can achieve the highest classification accuracy under the condition of minimum detection of warning molecules.
4, The warning molecules found in the present method are original and can effectively achieve accurate identification of toxigenic Aspergillus flavus, and the established detection warning molecules are highly sensitive, thereby achieving high-sensitivity detection and analysis.

BRIEF DESCRIPTION OF THE DRAWINGS

FIG. 4(a) is Survival analysis curve of a random forest model (ROC). FIG. 4(b) is Cross-validation results of the random forest model. FIG. 4(c) is Plot of variable importance screening results. FIG. 4(d) is Prediction accuracy of the random forest model.

FIG. 5(a)-(d) show robustness confirmation of the biological early warning molecules by an independent validation set. FIG. 5(a) is Total survival analysis curve of the random forest model (ROC). FIG. 5(b) is Plot of significant variables screened by the random forest model. FIG. 5(c) is Principal component analysis of high- and low-toxigenicity strains by using early warning molecules in the validation set. FIG. 5(d) is Correlation analysis of the toxigenicity values of strains predicted by using early warning molecules with the measured toxigenicity values of the strains.

FIG. 6(a)-(f) show Pearson correlation analysis correlating Aspergillus flavus toxigenicity and early warning molecules. FIG. 6(a) shows the correlation analysis between 5-methoxysterigmatocystin and toxigenicity, FIG. 6(b) shows the correlation analysis between the warning molecule A and toxigenicity, FIG. 6(c) shows the correlation analysis between the warning molecule B and toxigenicity, FIG. 6(d) shows the correlation analysis between versiconol and toxigenicity, FIG. 6(e) shows the correlation analysis between versicolorin_B and toxigenicity, and FIG. 6(f) shows the correlation analysis between the summed average of five warning molecules and toxigenicity.

FIG. 7 shows standard curves of aflatoxin B1 and 5 warning molecules for quantitative analysis of aflatoxin B1 and the warning molecules.

DESCRIPTION OF THE EMBODIMENTS

The present disclosure will be further described in detail below in combination with specific embodiments, in order to enable those skilled in the art to better understand the technical solutions of the present disclosure.

The abbreviations of the compounds involved in the present disclosure comprise: versiconol (VOH), versicolorin B (Ver B), aflatoxin B1 (AFB1), aflatoxin B2 (AFB2), and 5-methoxysterigmatocystin (5-MST).

In the following embodiments, a process for establishing a standard curve includes: 200 mg of *Aspergillus flavus* mycelia are weighed and added into a mortar and ground in liquid nitrogen, and then 5 mL of PBS buffer solution is added. The resulting solution is gradiently diluted to 0.01, 0.05, 0.1, 0.5, 1, 2, 5, 10, and 100 μg/mg of mycelium liquid to construct the standard curve.

Embodiment 1 Screening of Warning Molecules for Toxigenic Strains of Aflatoxin

Figure 1:
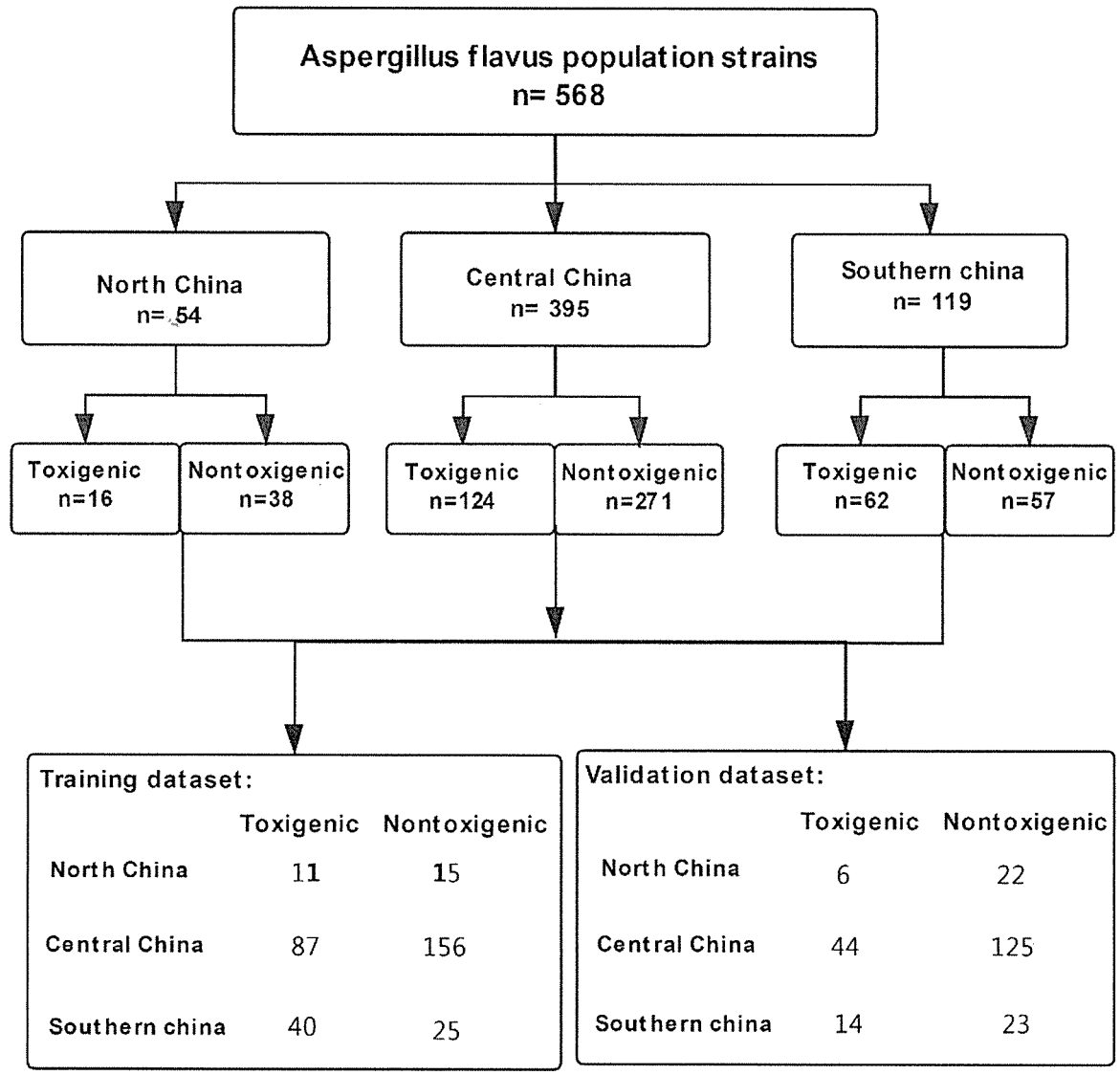
FIG. 1 is a sampling experimental design solution of toxigenicity screening for Aspergillus flavus population strain in China, wherein the sample is carefully selected according to the toxigenicity of strains and geographic and ecological origin.
Figure 2:
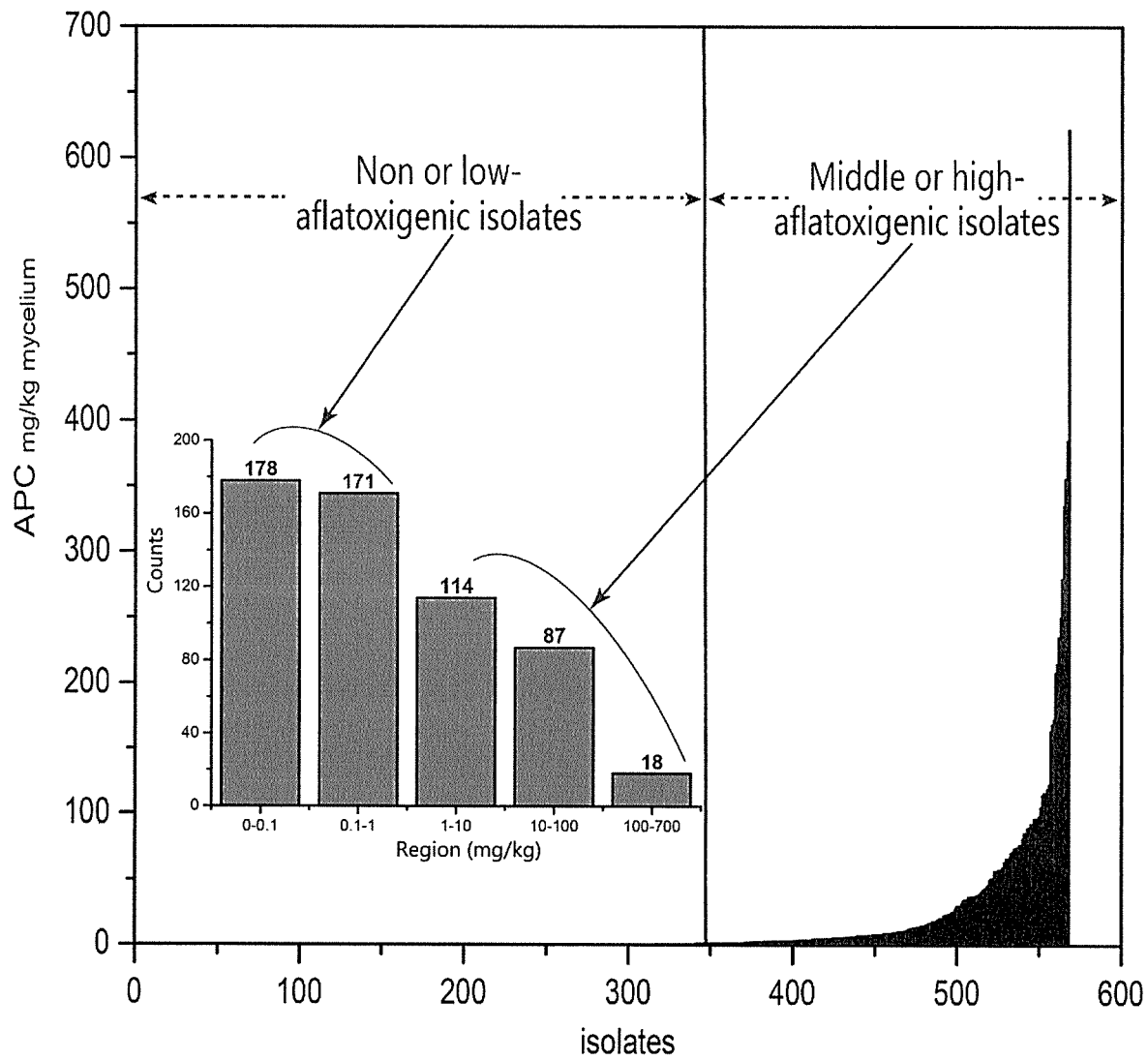
FIG. 2 shows classification of non-toxigenic, low-toxigenic and medium- or high-toxigenic Aspergillus flavus population strains.
Figure 3:
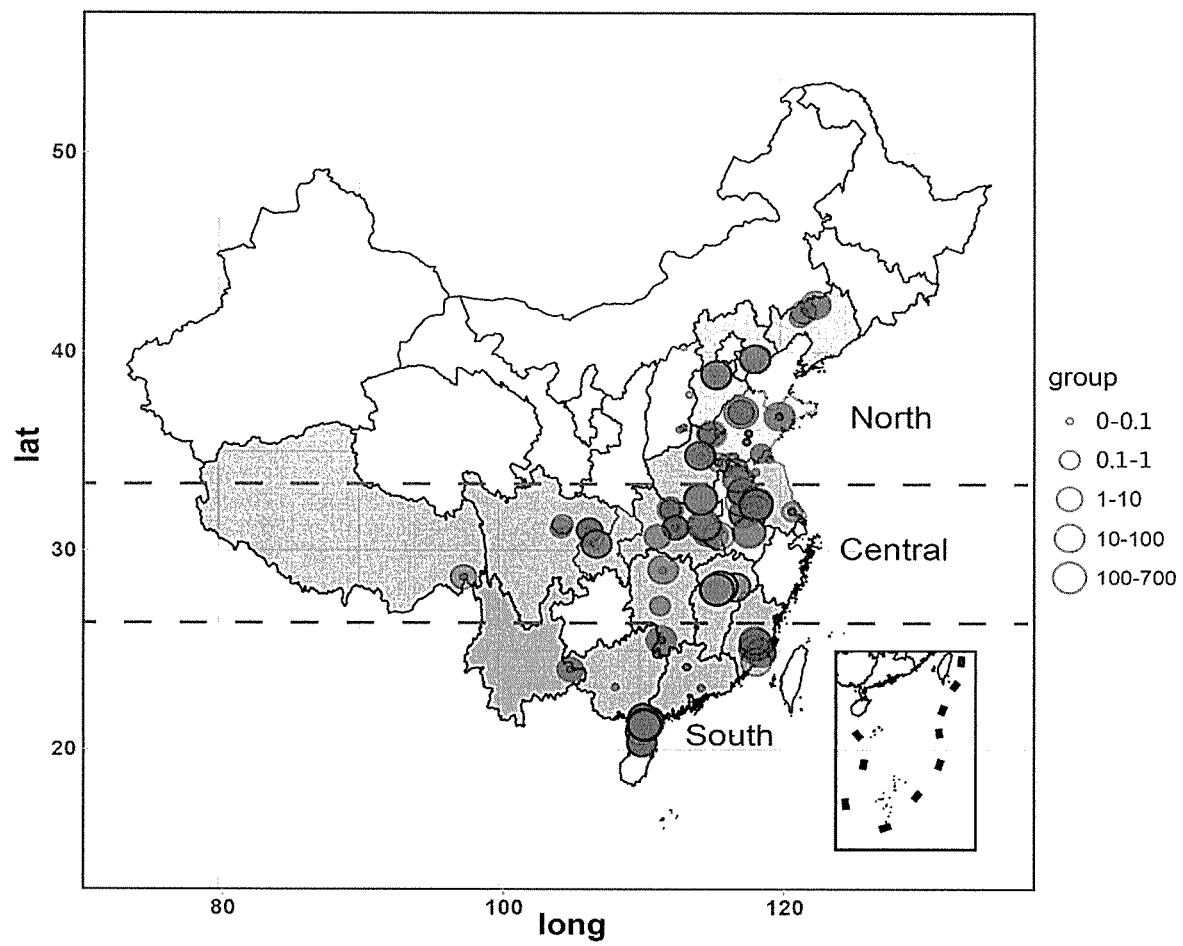
FIG. 3 shows regional division of the toxigenicity of Aspergillus flavus population strains in northern, central and southern regions of China.

The warning molecules that may effectively distinguish high- and low-toxigenicity strains were screened by systematically investigating the metabolic diversity properties of the *Aspergillus flavus* population, in combination with machine learning techniques, mainly including the following steps.

Selection of a representative sample: samples were prepared according to standard operating procedures. With reference to information of a strain bank of the *Aspergillus flavus* population, the strain was selected from the strain bank depending on the geographical origin.

Sample preparation: *Aspergillus flavus* was activated on a solid medium and cultured by using an Sabouraud liquid medium that contributed to the production of toxins, to obtain mycelial samples of different *Aspergillus flavus* strains.

Sample pre-treatment: a metabolome sample was quenched, mycelia were ground, and an extraction solution containing an internal standard was added for extraction. The extract was centrifuged at a high speed, and filtered with a filter membrane to yield a sample to be uploaded to a machine.

Sample detection: the aforementioned sample was subjected to detection and analysis by liquid chromatography-high resolution mass spectrometry for qualitative and quantitative analysis, to obtain the analytical results of the warning molecules. Internal standard substances were used in detection by liquid chromatography-high resolution mass spectrometer, and the internal standard substances were camphoric acid (a negative ion mode) and 2-chlorophenylalanine (a positive ion mode).

Generally, the qualitative analysis described above includes first-level, second-level and third-level qualitative analysis results. The first-level qualitative result is a result that the detected compound is verified by the standards and has completely matched information in primary and secondary mass spectrometry and consistent retention time. The second-level qualitative result is a result of a qualitative compound that has a 50% or higher matching score between the characteristic peaks extracted from the sample and the secondary mass spectrometry information in the public database. The third-level qualitative result is a result of a sample that has a deviation less than 5 ppm from the first-order accurate mass number of the compounds already reported in the study species.

The qualitative analysis in the disclosure includes: determining the mass deviation to be within 5 ppm, based on the accurate mass number of the primary mass spectrometry of the warning molecule; comparing the secondary mass spectrogram with the main characteristic ion peaks of the secondary mass spectrogram of the warning molecule (as shown in FIG. 11(*a*)-(*e*)) for qualitative analysis, specifically: comparing the secondary mass spectrogram with the secondary mass spectrogram of the warning molecule detected in *Aspergillus flavus* that we constructed beforehand, and comparing the similarity of the main characteristic ion peaks and their intensity ratios under the same mass spectrometry detection condition, wherein if there was high similarity, it was determined that these warning molecules were present in the sample; performing the quantitative analysis based on the pre-established standard curve of the chromatographic peak area/the peak area of the internal standard-warning molecule concentration, in combination with the internal standard substances.

After qualitatively obtaining the metabolite list, software Xcaliber 3.1 was used to extract and detect the peaks of the qualitative metabolites, to obtain a raw data list of the peaks. Metabonomic data preprocessing includes: the peaks were firstly extracted from raw data containing primary and secondary mass spectrometry information (which may be imported into Compound Discovery 2.1 for peak extraction from raw data), while the chemical molecular formula thereof was predicted, and then the peaks were aligned, and the accurate mass numbers in primary and secondary mass spectrometry were matched with the mass spectrogram database for qualitative analysis to obtain the raw data list of the peaks.

The specific process is stated below.

(1) Experimental Design, Sample Pre-Treatment, and Detection and Identification of Metabolite The representativeness of the sample is of vital importance, in order to screen a potential warning molecule of a toxigenic *Aspergillus flavus* strain to assess the risk of aflatoxin contamination. For this purpose, we carefully selected strains, as a sample, from a strain bank established from samples taken from 337 counties for this study, and the strains had different toxigenicity and were derived from the northern, central and southern regions. As shown in FIG. 1, the sampling experimental design solution for screening the toxigenicity of *Aspergillus flavus* population strains is as follows: according to the proportion of peanut cultivation and the ecogeographic type, we selected 68 strains from the northern region, wherein 33.8% of the strains were highly toxigenic and 66.2% of the strains were low- or non-toxigenic strains. From the central region, 413 strains were selected, wherein 42.6% of the strains were highly toxigenic strains and 57.4% of the strains were low- or non-toxigenic strains. From the southern region, 125 representative strains were selected, wherein 59.2% of the strains were highly toxigenic strains and 40.8% of the strains were low- or non-toxigenic strains. Metabolomic data acquisition was performed on these 568 samples, and these strains from different sources were randomly distributed during the sample preparation and data acquisition or subsequent marker screening, while meeting the requirements of the solution in FIG. 1. Among these, 334 samples were used as a training set to discover warning molecules and the remaining 234 samples were used as an independent validation set to assess the robustness of the screened warning molecules. The classification of non-toxigenic, low-toxigenic and middle or high-toxigenic *Aspergillus flavus* population strains is shown in FIG. 2. The rule for identification and classification of toxigenicity is: the strains were divided into five groups according to their toxigenicity values, in which a first group consisted of non-toxigenic strains with 0-0.1 mg/kg of mycelium, a second group consisted of low-toxigenic strains with 0.1-1 mg/kg of mycelium, a third group consisted of medium-toxigenic strains (1-10 mg/kg of mycelium), a fourth group consisted of medium- or high-toxigenic strains (10-100 mg/kg of mycelium), and a fifth group consisted of the high-toxigenic strains (100-700 mg/kg of mycelium), as shown in FIG. 2.

FIG. 3 shows the region division of the toxigenicity of *Aspergillus flavus* population strains in the northern, central and southern regions of China.

(2) The Experimental Method of Strain Culture and Sample Pre-Treatment

A PDA agar medium (Becton, Dickinson and company, France) was inoculated with the *Aspergillus flavus* conidia and the *Aspergillus flavus* conidia were incubated at 29±1° C. for 8-10 days. Spores were washed by using 0.1% of Tween-80 to obtain a spore suspension. Spores were counted by using a hemocytometer plate in combination with a microscope and the concentration of the spore suspension was calculated. A liquid medium with 0.25% of a yeast extract, 0.1% of $K_2HPO_4$, 0.05% of $MgSO_4\text{-}7H_2O$, and 10% of glucose, was prepared, and the pH of the medium was adjusted to 6.0. Then, 50 mL of the prepared liquid medium was subpackaged in a triangular culture flask and sterilized at high temperature for 20 min. The sterilized liquid medium was inoculated with the spores at $5\times10^5$ spores/mL, and the spores were incubated in a shaker at 180 rpm at 29±1° C. for 5 days, and filtered to collect the mycelial sample.

Quenching and pre-treatment of the sample: after obtaining the mycelial sample as described above, the mycelial sample was quickly filtered, rinsed with 10 mL of saline (0.9% (wt/vol) NaCl) at 4° C., and then quenched by using liquid nitrogen. The sample was stored in a freezer at −80° C. for drying, and then lyophilized by using a freeze dryer. 50 mg of the sample was weighed, and was subjected to extraction with 1 ml of an extraction solution containing an internal standard substance (methanol:acetonitrile:water=2:2:1), 5 steel beads were added, and then the sample was triturated by using a homogenizer. The sample was subjected to ultrasonic extraction in an ice bath for 10 min, and centrifuged at 20,000 rpm. The supernatant was transferred to a new EP tube. Then, another extraction solution (methanol:dichloromethane:ethyl acetate=1:1:1) was added to the EP tube containing the mycelial sample for the second extraction. Finally, the two extracts were mixed, centrifuged at 20,000 rpm for 10 min, filtered through a 0.22 um filter membrane into an injection vial and stored in a refrigerator at −20° C. to be uploaded to a machine.

(3) Mass Spectrometry Analysis

The conditions for mass spectrometry detection were as follows.

Chromatographic separation was performed on a high performance liquid chromatography (Dionex, Sunnyvale, CA, USA), wherein a chromatographic column is a $C_{18}$ reverse chromatographic column; mass spectrometry was performed by using an Orbitrap Fusion electrostatic orbitrap high-resolution mass spectrometer (Thermo Scientific, USA), and the liquid chromatographic method uses a mobile phase A: a mixed solution of methanol/water (95/5, v/v, containing 0.1% formic acid and 10 mM ammonium formate) and a mobile phase B: a mixed solution of water/methanol (95/5, v/v, containing 0.10% formic acid and 10 mM ammonium formate). The gradient elution procedure was: 0-1 min: 85% of the phase A, 1-3 min: 85%-50% of the phase A, 3-5 min: 50%-30% of the phase A, 5-10 min: 30%-0% of the phase A, 10-13 min: 0% of the phase A, 15 min: 0-85% of the phase A, 15-20 min: 85% of the phase A (the balance is the phase B). The conditions for the described high-resolution mass spectrometry: ion source heating temperature of 300° C.; spray voltage: 3.5 Kv in a positive ion mode and 3.0 Kv in a negative ion mode; sheath gas of 40 Arb; auxiliary gas of 5 Arb; ion transport capillary temperature of 320° C. and capillary voltage of −1.9 Kv. The main first-order accurate mass number full scan parameters were as follows: Orbitrap was selected as a detector, the resolution was selected as 120,000 FWHM (a half-peak width), the scan range was 100-1,000 m/z, the automatic gain control was set to be $1.0e^6$, and the injection time was 100 ms. The main filtering parameters between the primary and secondary scans were as follows: the intensity threshold was $1.0e^4$, the number of charge was 1-2, and dynamic exclusion was set to be 1. A top speed mode was selected for data dependent acquisition, and the cycle time was set to be is. The main secondary mass spectrometry scan (dd-ms$^2$) parameters were as follows: a higher energy collision induced dissociation (HCD) mode was selected as a fragmentation mode, and the collision energy was set to be 35 ev in a positive ion mode and 30 ev in a negative ion mode. The detector type was Orbitrap, the resolution was set to be 30,000 FWHM, and the automatic gain control was set to be $5.0e^4$. The maximum injection time was set to be 100 ms, and the quadrupole isolation width was set to be 1 Da.

(4) Compound Identification

The raw mass spectrogram data were imported into the metabolome data processing software Compound Discovery 2.1, and more than 1483 metabolic features were detected. We manually identified a total of 217 metabolites by comparing the online database with the local database in combination with the relevant literature information of the studied species. In addition, we sorted all the extracted metabolic features based on a peak area size, and the metabolic features not identified in this study were still retained and added to a data matrix for subsequent multivariate statistical analysis. The compounds were characterized by secondary matching scores obtained through comparing the mzCloud database. The local database was also compared.

(5) Screening of Important Warning Molecules

The metabolome dataset from 334 randomly selected above *Aspergillus flavus* strains was used as a model training set. A large number of candidate differential warning molecules were first screened by using univariate and simple multivariate statistical analysis tools. Based on more than 30 significant warning molecules screened above, we further trained a random forest model as a classifier to generate a receiver operator characteristic (ROC) curve for the screening of the significant warning molecules.

Figure 4A:
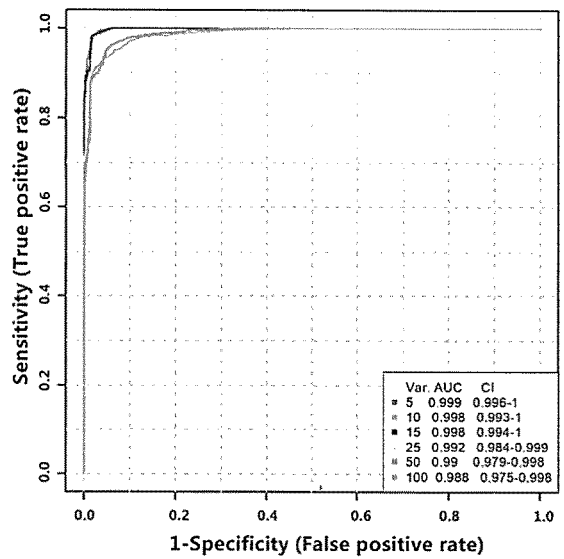
FIG. 4(a)-(d) show screening of biological warning molecules for the toxigenic Aspergillus flavus by a random forest algorithm.
Figure 4B:
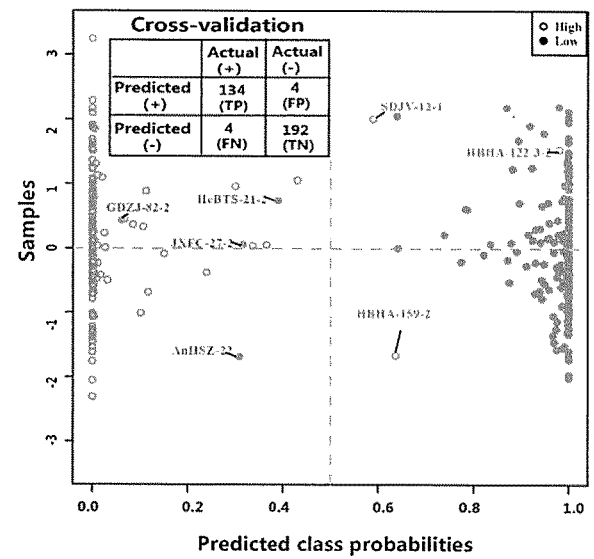
Figure 4C:
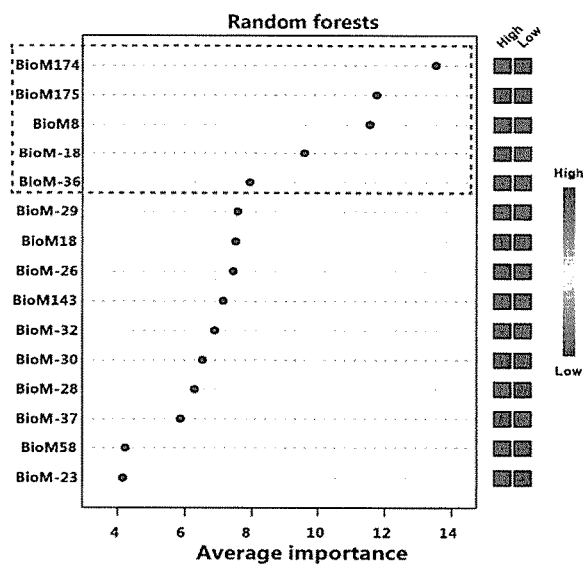
Figure 4D:
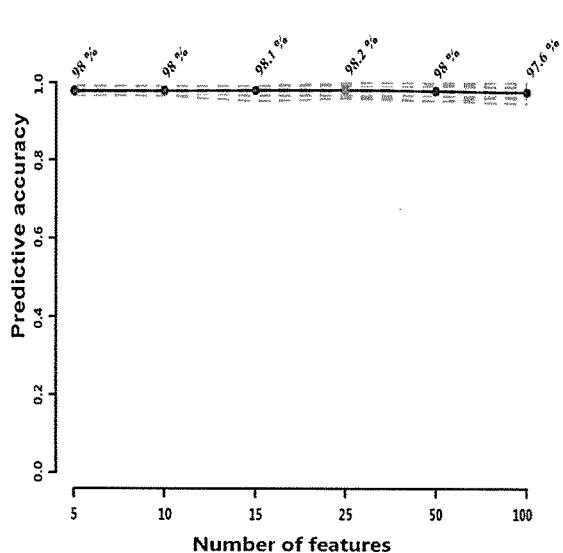

To screen the most effective warning molecule for the toxigenic *Aspergillus flavus*, we evaluated the importance of each candidate warning molecule to the model and the warning molecules were sorted. FIG. 4(c) shows the 15 most important candidate warning molecules screened by the model, including: BioM174 (a warning molecule A), BioM8 (5-Methoxysterigmatocystin), BioM175 (a warning molecule B), BioM-18 (Versiconol), BioM-36 (Versicolorin_B), BioM-26 (Versicolorone), BioM-29 (Hydroxyvers-icolorone), BioM18 (O-Methylsterigmatocystin), BioM-32 (Oxoaverantin), BioM-28 (Hydroxyversicolorone), and the like. The performance of the models constructed with a different number of variables is shown in FIG. 4(a). Model 1 is a model constructed by using the five most important variables, with the shaded area (AUC) under the receiver operator characteristic curve of 0.999, and a confidence interval (CI) of 0.996-1. This indicated that in the training set, the strains with high and low toxigenicity were classified by the most important top five variables. FIG. 4(b) showed the confirmatory results of the performance of the model constructed with the most important five variables. According to a confusion matrix (cross-validation) variance Monte Carlo sampling method, ⅔ of the data samples in the training set were randomly selected for the construction of the classification model, and ⅓ of the samples were used for the internal model evaluation of the model. An accuracy of 97.8% was achieved for classification and identification of highly toxigenic strains. The accuracy of the model was evaluated and it was found that the classification accuracy of five most important warning molecules achieved 97.8%. As the variable increases, the predicted classification accuracy of the model did not increase significantly, as shown in FIG. 4(d).

The remaining 234 samples were further utilized as an independent validation set to validate the warning molecules, and the validation results showed that the five warning molecules were also screened in the independent validation set and ranked in the top five (as shown in FIG. 5(a)-(d)), and the model constructed by these five warning molecules had the best prediction accuracy.

The XGBoost model parameters and prediction accuracy are shown in Table 3 below.

TABLE 3

XGBoost model parameters and prediction accuracy

| Model | Features | Numbers of tree | Accuracy |
|---|---|---|---|
| 1 | 5-Methoxysterigmatocystin, warning molecule B, Versicolorin_B | 100 | 96.6% |
| 2 | 5-Methoxysterigmatocystin, warning molecule B, Versicolorin_B | 1 | 94.25% |
| 3 | 5-Methoxysterigmatocystin and warning molecule B | 1 | 89.66% |
| 4 | warning molecule B and Versicolorin_B | 1 | 94.25% |
| 5 | warning molecule B | 1 | 91.95% |

Figure 10:
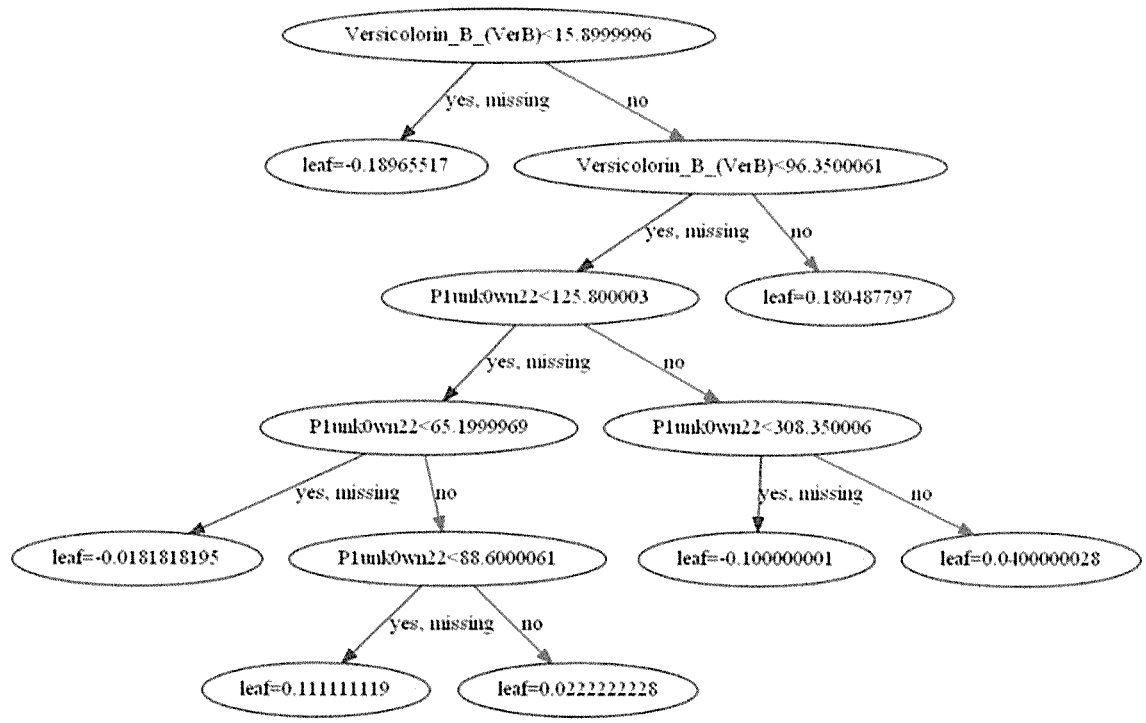
FIG. 10 shows Single-tree XGBoost established by a warning molecule B and Versicolorin_B.
Figure 11A:
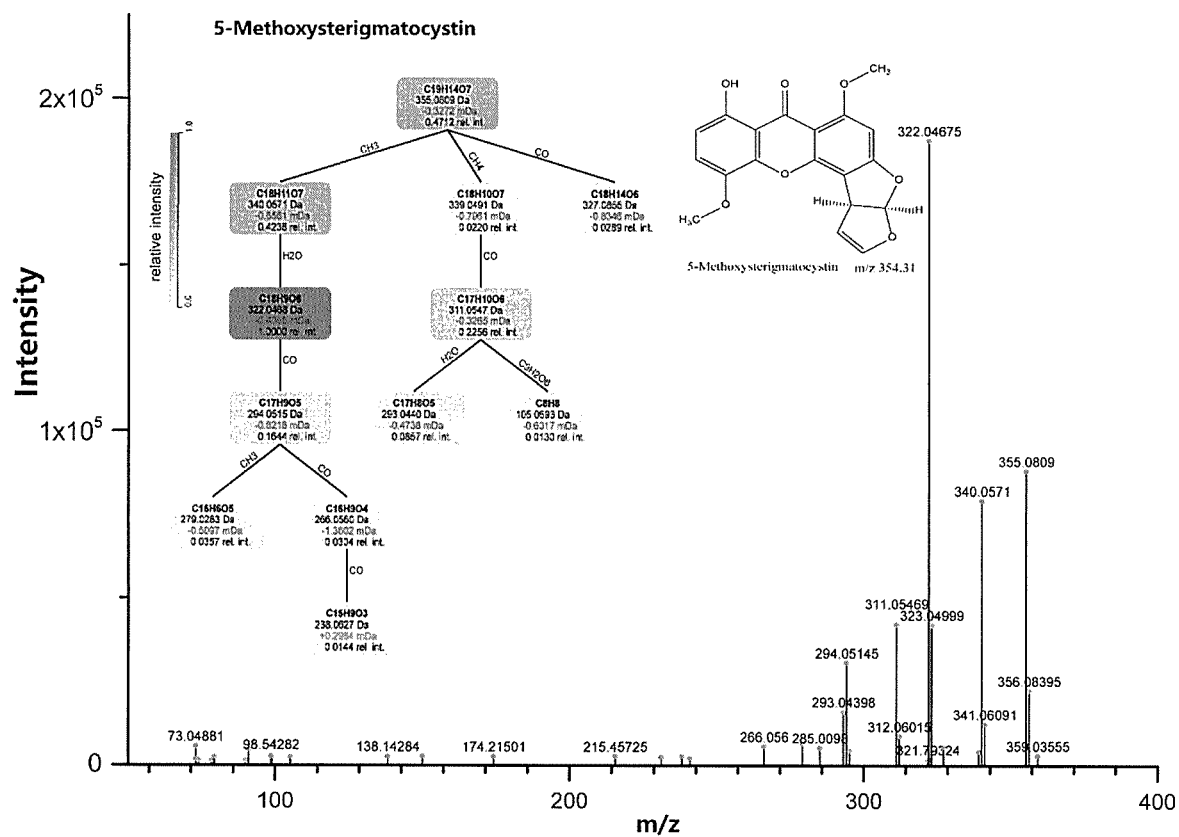
FIG. 11(a)-(e) show the secondary mass spectrogram and multi-level mass spectrogram fragmentation ion tree of 5 warning molecules for the qualitative analysis and comparison of the warning molecules, that is, to compare whether the major fragmentation ions in the secondary spectrogram of the measured molecules in the samples could be matched with the given secondary spectrogram.
Figure 11B:
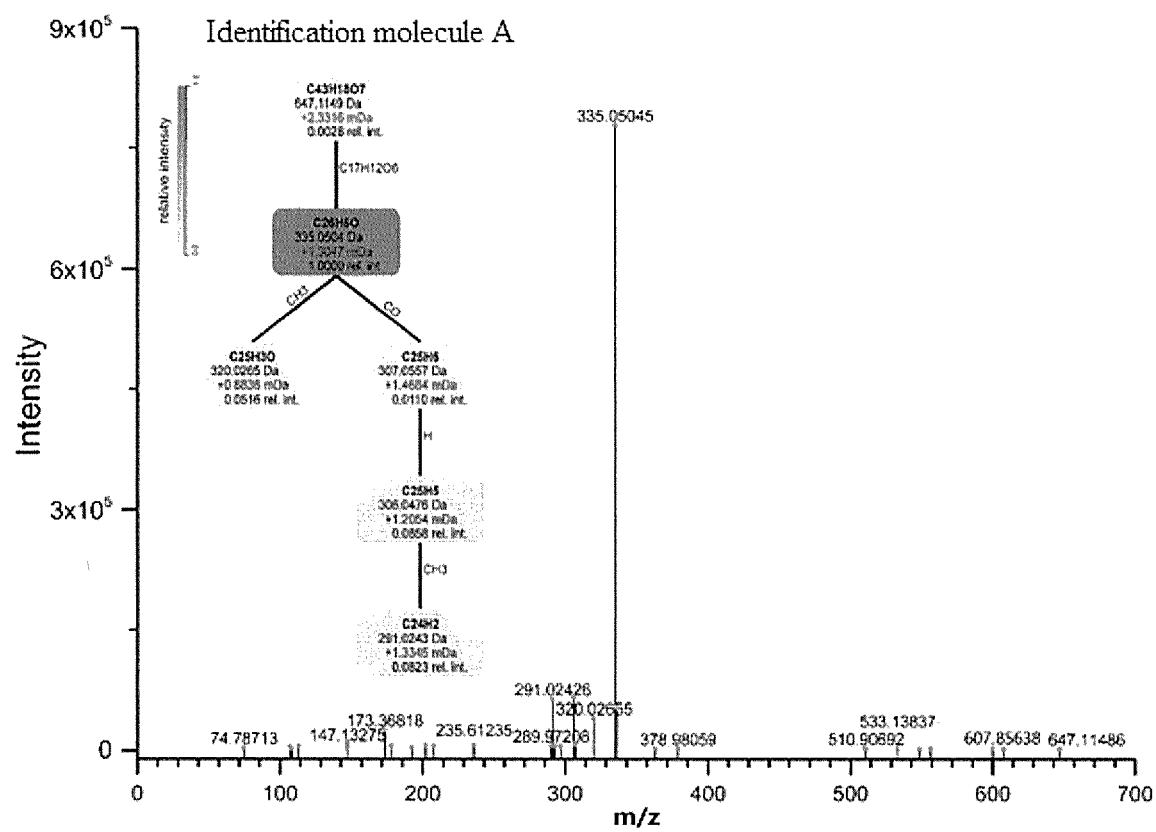
Figure 11C:
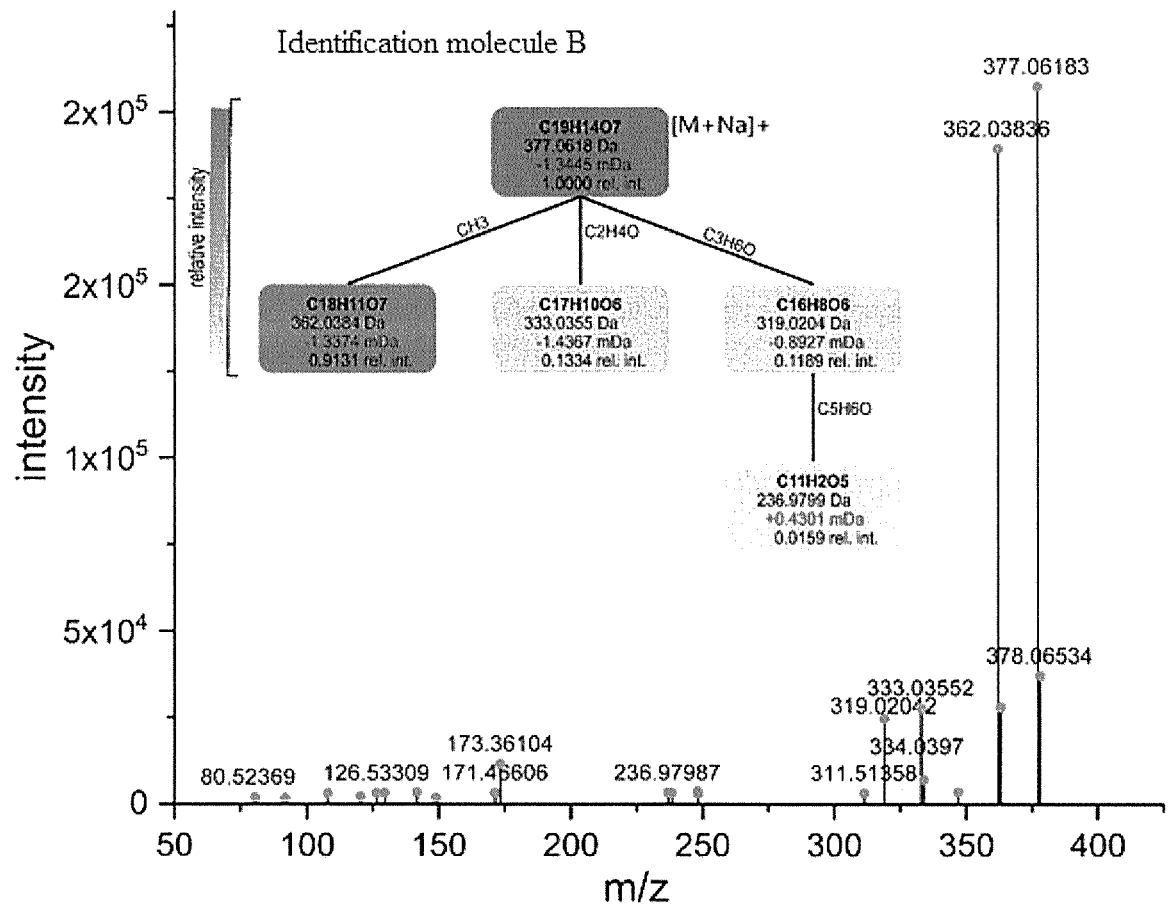
Figure 11D:
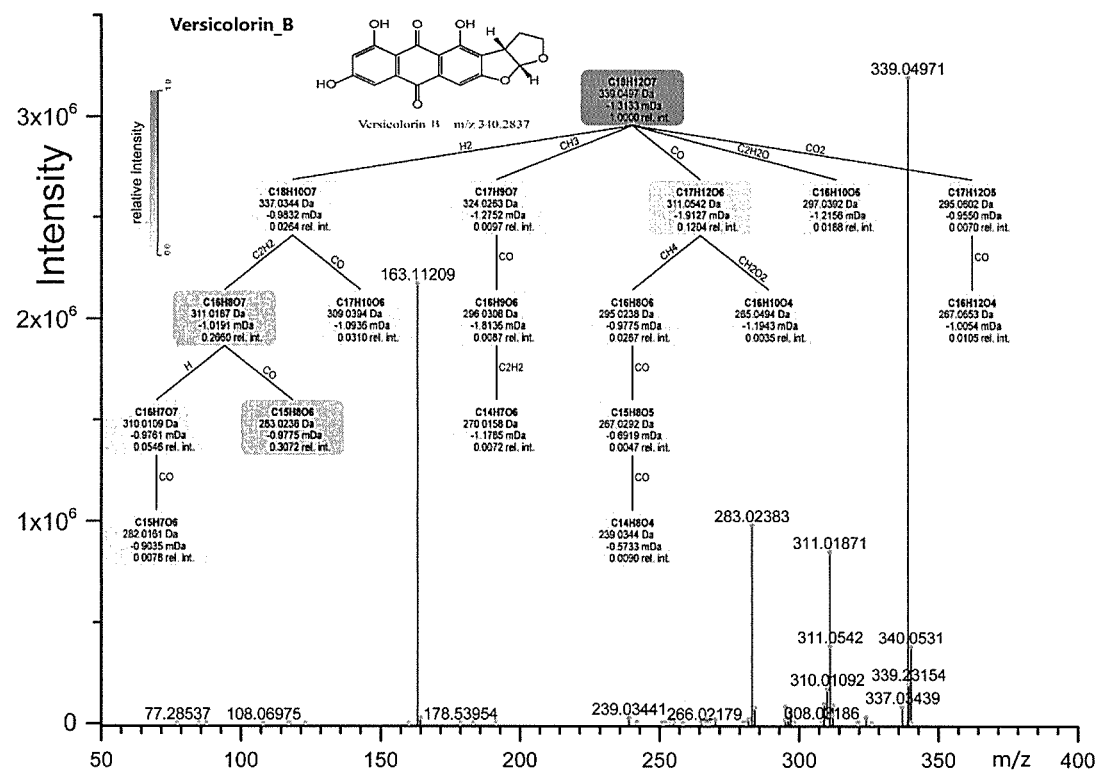
Figure 11E:
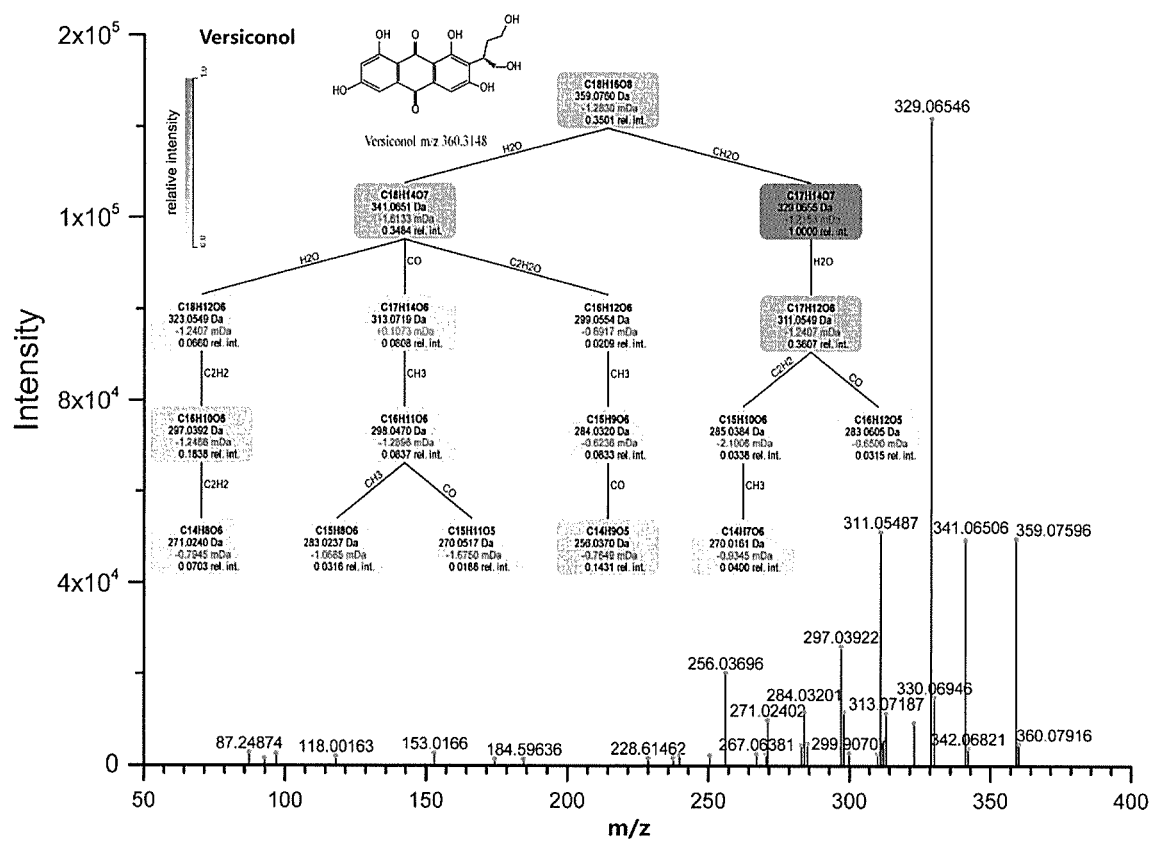

FIG. 10 showed the Single-tree XGBoost simple decision tree model established by the warning molecule A and Versicolorin_B, with an accuracy of 94.25%.

(6) Further Method Validation

To ensure the reliability and general applicability of the results, methodological corroboration was performed by a detection limit, a quantification limit, precision, linearity and specificity. The detection limit is calculated when the signal-to-noise ratio is greater than 3, and the quantification limit is calculated when the signal-to-noise ratio is greater than 10. The measurement error was calculated by using intra-day continuous injection and inter-day non-continuous 3 days to assess precision of the methods. Linearity range was assessed by weighing 200 mg of mycelia, preparing crushed *Aspergillus flavus* mycelia, and diluting to make a standard curve with a gradient of 0, 0.01, 0.05, 0.1, 0.5, 1, 2, 5, 10, and 100 µg/mg. The results are shown in FIG. 7.

The detection limit and quantification limit for aflatoxin and the warning molecules for toxigenic *Aspergillus flavus* were 0.003-0.20 and 0.012-0.50 µg/mg (mycelia), respectively, with intra-day and inter-day precision of 0.02-0.56 and 0.06-0.44, and $R^2$ of 0.9993-0.9999. See Table 2 below for details. The quantitative standard curves for aflatoxin B1 and toxigenic warning molecules were shown in FIG. 7.

TABLE 3

Methodological corroboration parameters for warning molecules

| warning molecule | Regression equation | $R^2$ | Linearity range (µg/mg) | Detection limit (µg/mg) | Quantification limit (µg/mg) | RSD % (intra-day precision) | RSD % (inter-day precision) |
|---|---|---|---|---|---|---|---|
| Aflatoxin $B_1$ | Y = 12044.5X + 1.1 *10$^7$ | 0.9995 | 0.1-100 | 0.003 | 0.012 | 0.10 | 0.10 |
| 5-Methoxysterigmatocystin | Y = 317.3X − 114190.2 | 0.9999 | 0.5-100 | 0.13 | 0.43 | 0.06 | 0.08 |
| warning molecule A | Y = 58.4X − 58049.3 | 0.9999 | 0.5-100 | 0.20 | 0.50 | 0.56 | 0.44 |
| warning molecule B | Y = 248.3X + 107297.8 | 0.9997 | 0.5-100 | 0.07 | 0.23 | 0.07 | 0.10 |
| Versicolorin_B | Y = 232.9X − 142191.5 | 0.9993 | 0.1-100 | 0.06 | 0.23 | 0.11 | 0.12 |
| Versiconol | Y = 62.5X + 39562.3 | 0.9998 | 0.1-100 | 0.10 | 0.40 | 0.02 | 0.06 |

RSD: Relative Standard Deviation

The specificity of the biological warning molecules discovered in this study was assessed by analyzing the metabolomes of other fungi isolated from peanut rhizosphere soil and present in agricultural products, and comparing the presence or absence of biological warning molecules in other fungi. By comparing 15 other fungi isolated from peanut rhizosphere soil and peanut samples, we found that the warning molecules for toxigenic *Aspergillus flavus* were not found in other fungi, but only present in the toxigenic *Aspergillus parasiticus*. It was shown in Table 1 below. This indicated that the warning molecules reported in the present patent may have good specificity for distinguishing toxigenic fungi at the subspecies level. This useful study may be extended to other toxigenic fungi as well.

TABLE 2

Results of specificity assessment of 15 different fungal strains isolated from rhizosphere soil

| Strains | Species | 5-methoxysterigmatocystin | warning moleculeA | warning moleculeB | versiconol | versicolorin_B |
|---|---|---|---|---|---|---|
| AnHHF-33 | Aspergillus oryzae | − | − | − | − | − |
| HeBHD-1 | Aspergillus oryzae | − | − | − | − | − |
| HuBLT-3 | Aspergillus oryzae | − | − | − | − | − |
| CJ-3-3 | Aspergillus ochraceus | − | − | − | − | − |
| BNCC336184 | Aspergillus ochraceus | − | − | − | − | − |
| HuBzhx-43 | Aspergillus fumigatus | − | − | − | − | − |
| LNCT-4 | Aspergillus parasiticus | + | + | + | + | + |
| BNCC340687 | Fusarium moniliforme | − | − | − | − | − |
| FJQ2H-4 | Rhizopus oryzae | − | − | − | − | − |
| GDHZ-1 | Pichia guilliermondii | − | − | − | − | − |
| GXWM-1 | Penicillium janthinellum | − | − | − | − | − |
| D83 | Trichoderma spp. | − | − | − | − | − |
| XZ-2-9 | Trichoderma spp. | − | − | − | − | − |
| XZ-11-5 | Trichoderma spp. | − | − | − | − | − |
| BNCC143078 | Fusarium oxysporum | − | − | − | − | − |

In the present disclosure, the content of 5 molecules described above and the toxigenicity value of *Aspergillus flavus* were measured, and the data were normalized to take a log value, and then subjected to spearman correlation analysis to obtain the above results. The correlations between each warning molecule and the toxigenicity of *Aspergillus flavus* were warning molecule A ($r=0.98$), warning molecule B ($r=0.91$), 5-methoxysterigmatocystin ($r=0.94$), versiconol ($r=0.83$), and versicolorin_B ($r=0.82$), respectively (as shown in FIG. 6(*a*)-(*f*)).

According to the present disclosure, representative *Aspergillus flavus* population strains are selected on a large scale for metabolome research, and a combined machine learning analysis method is used to screen out some brand-new warning molecules and their combinations are verified. Meanwhile, methodological corroboration and specificity assessment are performed on the general applicability of the warning molecules, and practical application was carried out, thereby achieving a good early classification and identification effect, providing original biological warning molecules for the early warning of toxigenic aflatoxin in agricultural products. This study uses advanced metabolomics technology combined with advanced machine learning differential screening technology for the development of mycotoxin early warning molecules for the first time, providing a research example for early warning of agricultural product quality and safety in China, with important reference values in theoretical research and practical application.

Embodiment 2 Early Warning Study of Toxigenic *Aspergillus flavus* in Agricultural Products There is a neglected problem in the current risk assessment process of actual peanut samples, that is, usually, whether the aflatoxin in the sample exceeds the standard is only detected, and the potential risk of samples that do not exceed the standard is still poorly understood. It is assumed that if the peanut samples are infested with *Aspergillus flavus*, humidity and other conditions are not suitable for the growth of *Aspergillus flavus, Aspergillus flavus* is temporarily in a dormant state, and aflatoxin in the peanut samples is not exceed the standard at this time, or even can not be detected. Once the temperature and humidity conditions are suitable, such samples will face a great risk of aflatoxin contamination.

To solve the above-mentioned problems, we applied the above developed warning molecules for toxigenic *Aspergillus flavus*. The peanut samples in which the detected aflatoxin content did not exceed the standard were added to a mold selection medium and placed in an incubator at 29° C. with a humidity of 90% for incubation. The suspected contaminated samples will grow mold visually. The suspected samples were subjected to sample pre-treatment to extract the warning molecules for toxigenic *Aspergillus flavus*, and then these warning molecules were analyzed and detected to achieve effective differentiation between contaminated and uncontaminated samples through chemometrics methods.

Therefore, according to the present disclosure, whether the sample has been contaminated by the toxigenic *Aspergillus flavus* before the toxin exceeds the standard can be determined in a short time by early detection for warning molecules for the toxigenic *Aspergillus flavus*. FIG. 8(*a*) is a recommended workflow for early detection of toxigenic *Aspergillus flavus* in actual peanut samples. Specifically, during the aflatoxin risk assessment process of actual agricultural products such as peanuts, the samples that exceeded the standard were screened out according to the detected aflatoxin monitoring value, and these samples were considered as high-risk samples. Then, the samples that did not exceed the standard or were not detected were subjected to an accelerated microbial growth experiment to screen out the suspected samples with *Aspergillus* growth. For these samples, early detection of warning molecules was carried out in the early stages of culture, and risk assessment and discrimination were performed according to the established early warning model or the developed simple and intuitive decision workflow.

Figure 8A:
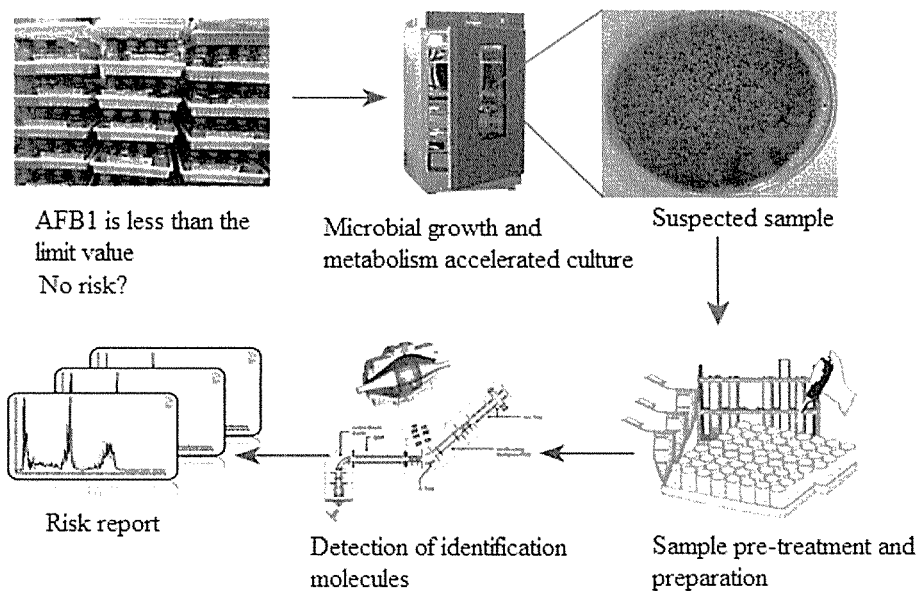
FIG. 8(a) shows a workflow for early warning by monitoring the metabolic warning molecules for the toxigenic Aspergillus fungus.
Figure 8B:
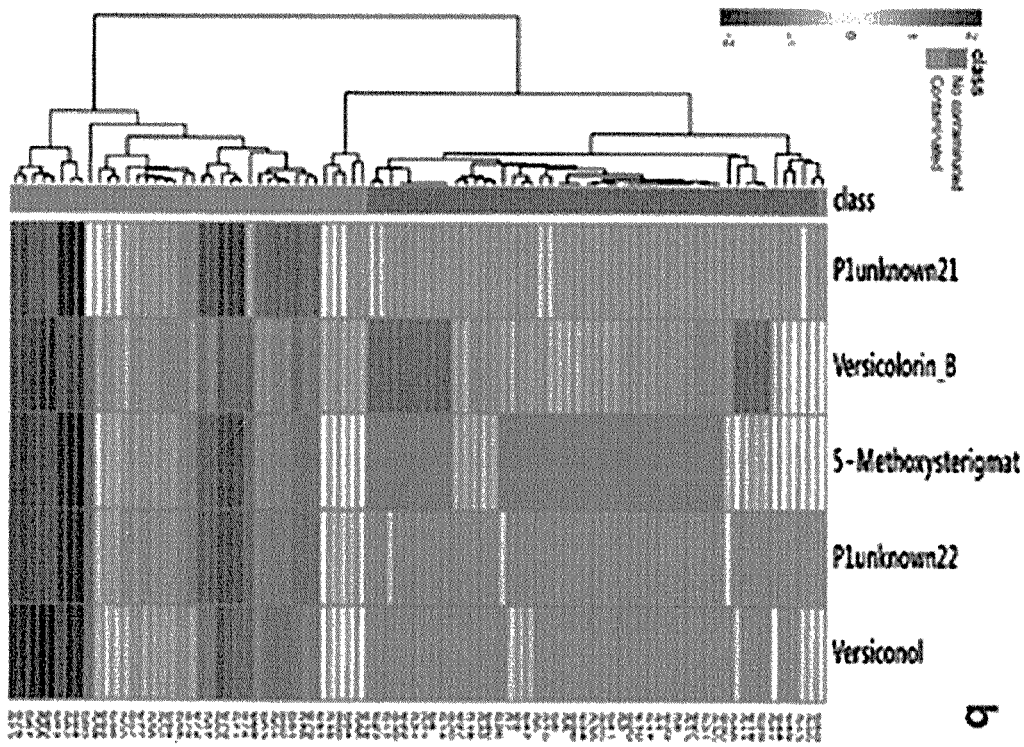
FIG. 8(b) shows a heat map showing the warning molecules effectively distinguishing 86 suspected samples.
Figure 9A:
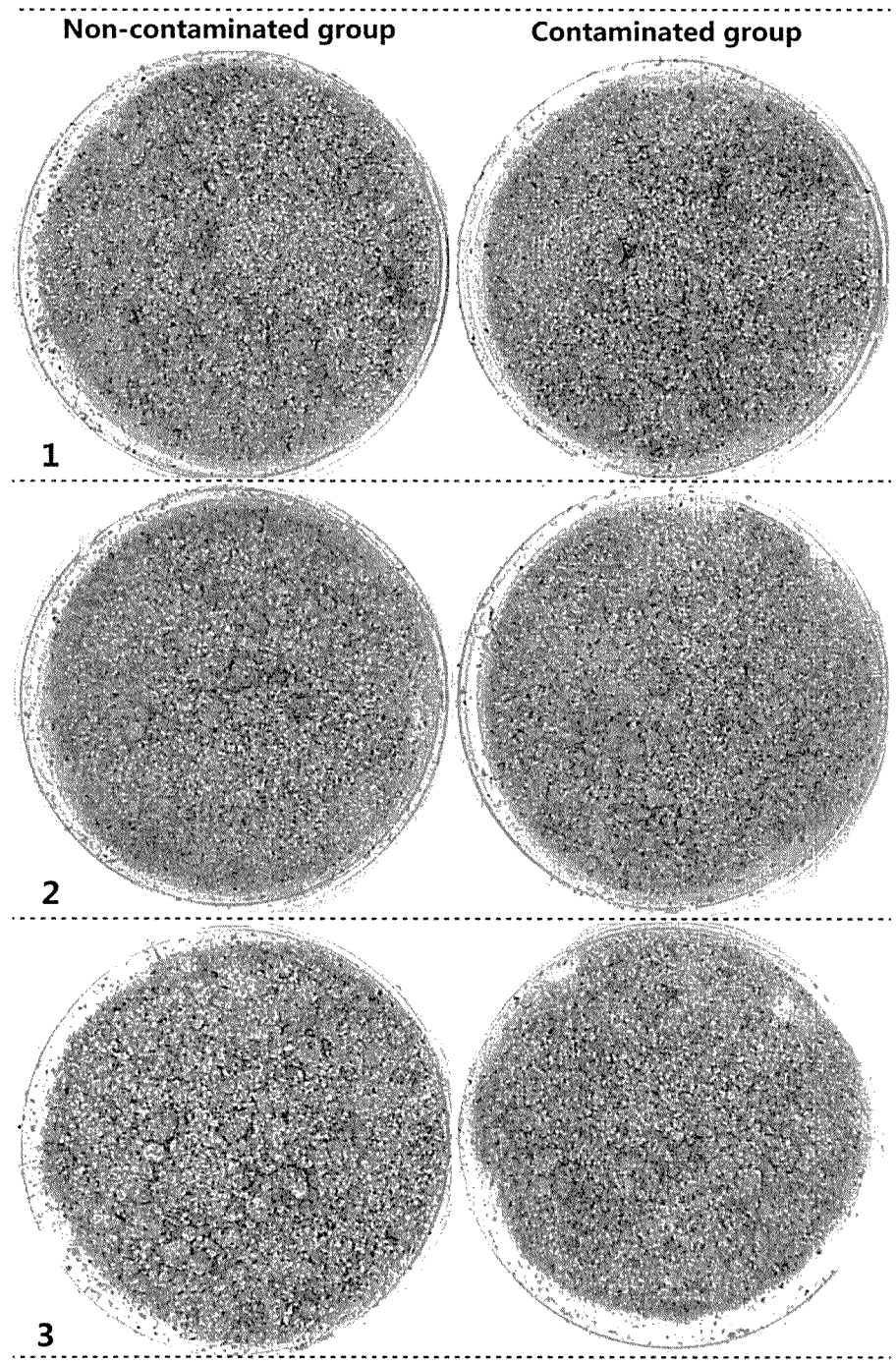
FIG. 9(a)-(d) show a dynamic phenotypic change graph of uncontaminated peanut samples and peanut samples contaminated with toxigenic Aspergillus during 13 days of incubation.
Figure 9B:
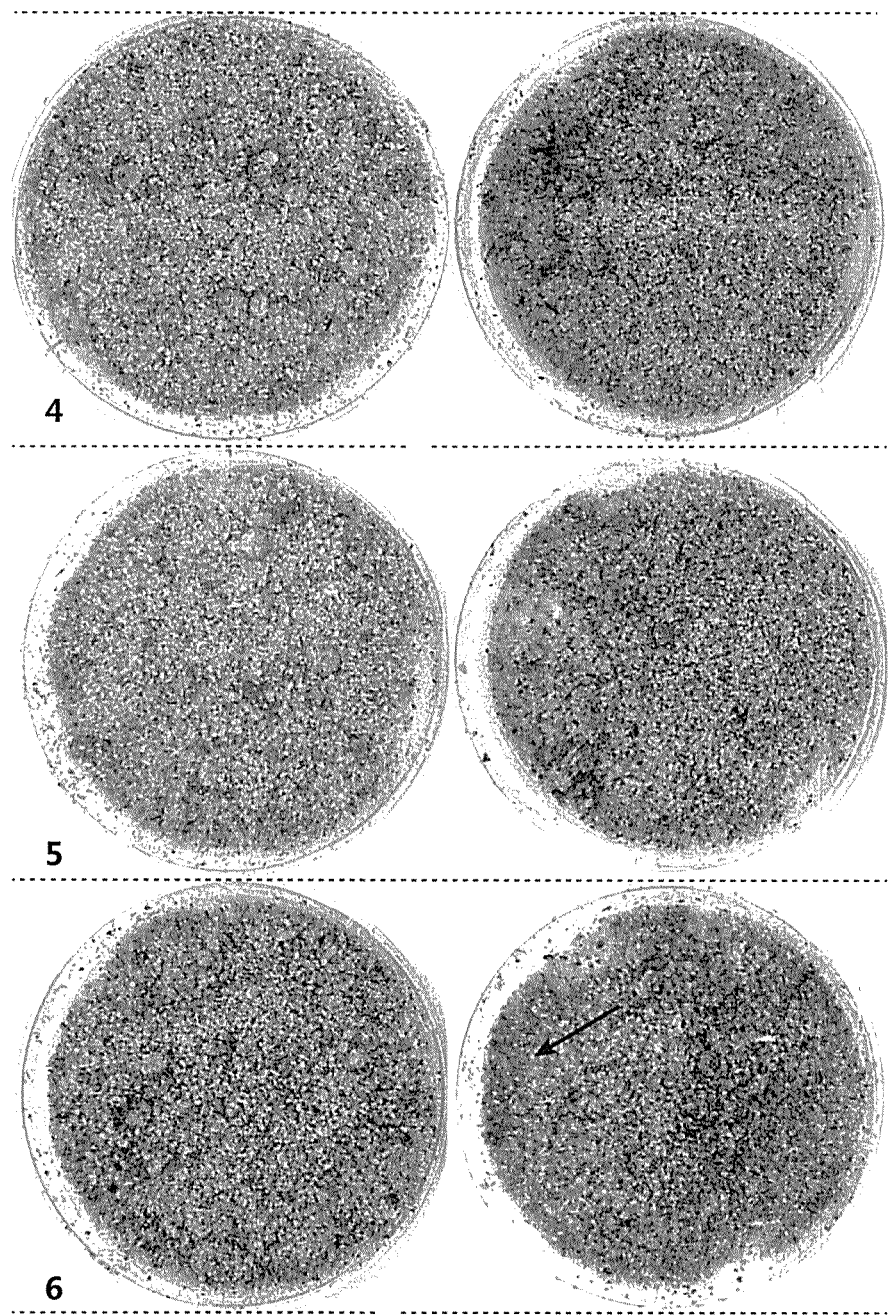
Figure 9C:
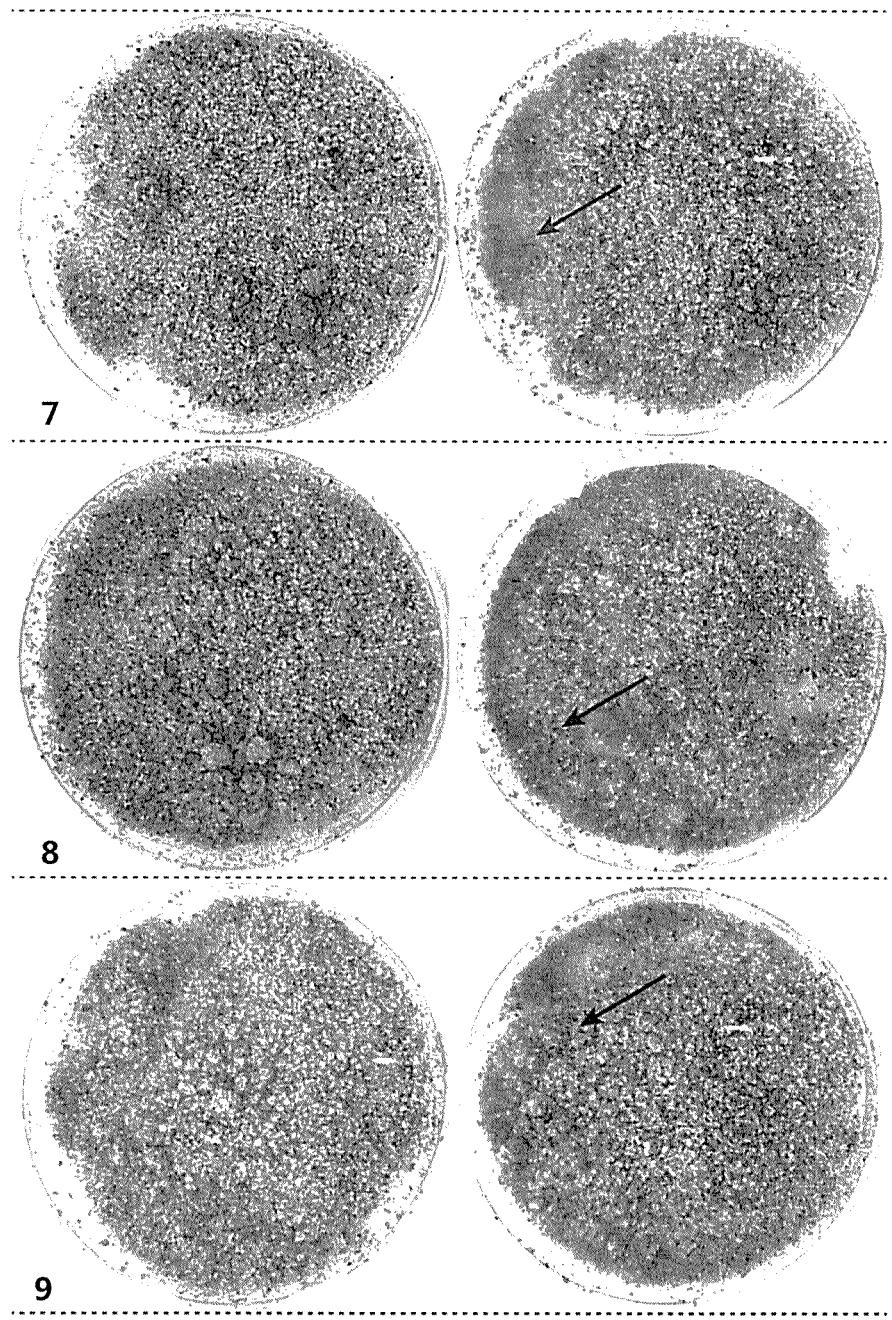
Figure 9D:
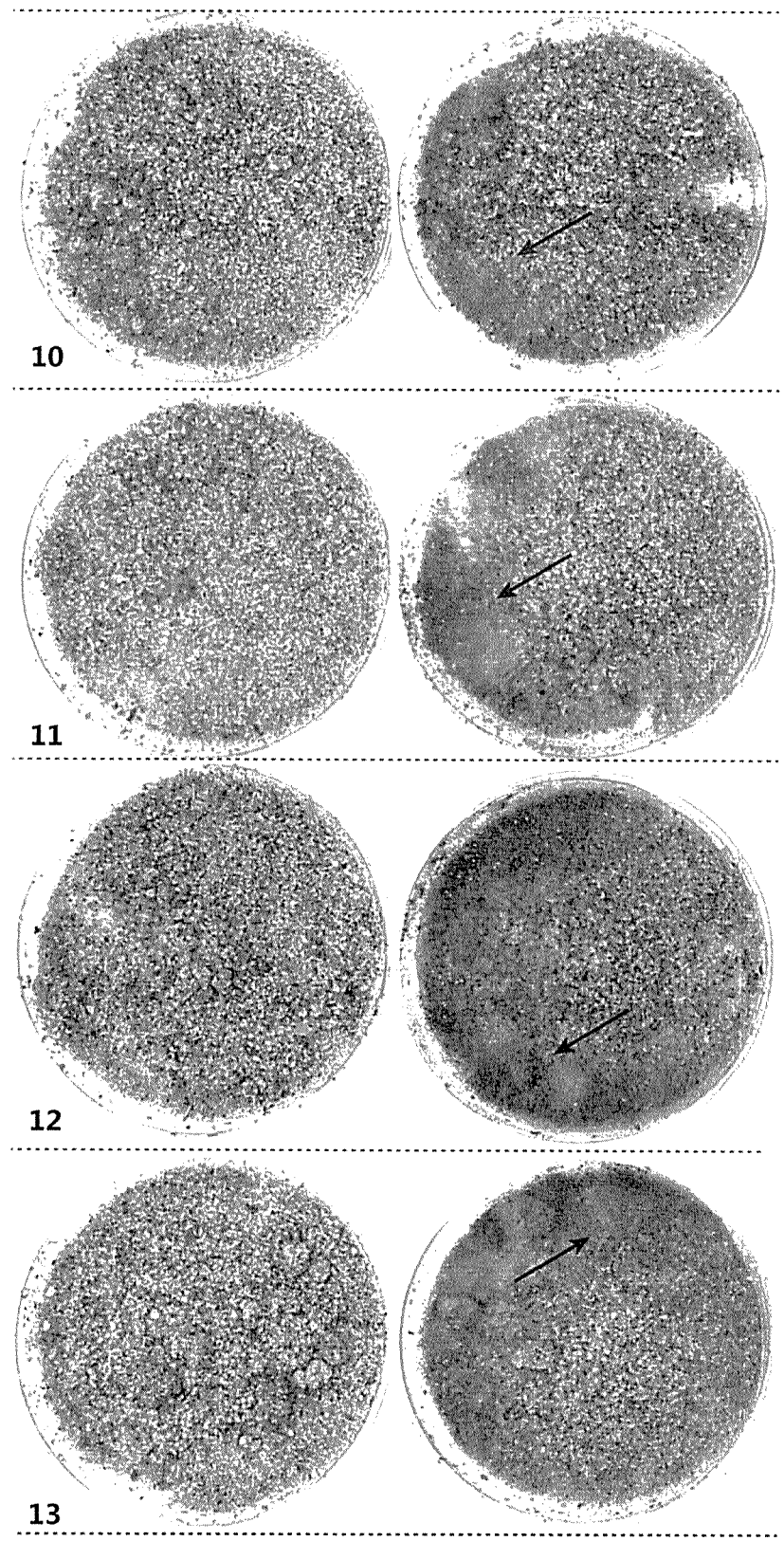

FIG. 8(b) shows that after cultivating and screening 429 samples of peanuts that did not exceed the standard, the samples with mold growth were identified as suspected samples. 86 suspected peanut samples were screened, and the warning molecules for toxigenic *Aspergillus flavus* were detected. The hierarchical clustering analysis in multivariate statistical analysis software such as R language software package can effectively classify the samples contaminated with toxigenic *Aspergillus flavus* and the samples contaminated with non-aflatoxigenic fungi. 39 samples among these were found to be contaminated with toxigenic *Aspergillus flavus*, and the results are shown in the heat map of FIG. 8(b).

The above are only the preferred embodiments of the present disclosure. Several improvements and changes can be made for those of ordinary skill in the art, without departing from the inventive concept of the present disclosure. For example, the toxigenic *Aspergillus flavus* described in the application may be extended to the category of toxigenic microorganisms, which have similar research ideas to the disclosure, and also belong to the protection scope of the present disclosure.

What is claimed is:

1. An early warning method before the occurrence of aflatoxin contamination, comprising the following steps: weighing a quantitative sample, extracting toxins from the sample to obtain a sample extract, and subjecting the sample extract to detection and analysis by liquid chromatography-high resolution mass spectrometer, collecting mass spectrometry information, and performing qualitative analysis based on the mass spectrometry information to obtain qualitative results of versiconol (VOH), versicolorin B (Ver B), 5-methoxysterigmatocystin (5-MST), a warning molecule A and a warning molecule B, and according to its corresponding chromatographic peak area in combination with an internal standard, performing quantitative analysis based on a standard curve of the chromatographic peak area of each warning molecule/the peak area of the internal standard-warning molecule concentration to obtain quantitative results of these warning molecules;

wherein, the qualitative analysis is performed by determining primary and secondary mass spectrometry information of the warning molecules in the sample, comparing the accurate mass number in the primary mass spectrometry of each warning molecule with a theoretical value thereof to obtain a deviation of the mass spectrometry being within 5 ppm, and then comparing main characteristic ion peaks of the secondary mass spectrometry in combination with the secondary mass spectrometry information;

wherein a theoretical value of accurate mass number of the warning molecule A is 647.11147, and a measured value of accurate mass number of the warning molecule A is 647.11469, a theoretical value of accurate mass number of the warning molecule B is 377.06289, and a measured value of accurate mass number of the warning molecule B is 377.06238, main characteristic peaks in a secondary mass spectrum of the warning molecule A comprise 335.05045 Da, 320.02655 Da, and 291.0243 Da;

main characteristic peaks in a secondary mass spectrum of the warning molecule B comprise 362.03836 Da, 333.0355 Da, and 319.0204 Da;

a risk of aflatoxin contamination of the sample is assessed to find a aflatoxin contamination sample including toxigenic *Aspergillus flavus*, aflatoxin or a combination thereof by performing modeling with a chemometrics method by using a content of the warning molecule A, or a content of the warning molecule B, or a content of one or more of the warning molecule A and the warning molecule B and one or more of versiconol (VOH), versicolorin B (Ver B) and 5-methoxysterigmatocystin (5-MST) as a variable to obtain a classification prediction model, inputting the quantitative results of the warning molecules for a toxigenic strain of *Aspergillus flavus*, and outputting a risk assessment result based on the classification prediction model.

2. The method according to claim 1, wherein the chemometrics method is a multivariate statistical analysis method including hierarchical cluster analysis, least partial square orthogonal projection, and random forest.

3. The method according to claim 1, wherein after the sample is cultured for 3-4 days, the sample is taken for detection of warning molecules for toxigenic *Aspergillus flavus*, and the quantitative values of versiconol (VOH), versicolorin B (Ver B), 5-methoxysterigmatocystin (5-MST), the warning molecule A and the warning molecule B are input into the classification prediction model to predict aflatoxin risk.

4. The method according to claim 1, comprising screening a suspected sample, pre-treating the screened suspected sample, detecting the warning molecules for toxigenic *Aspergillus*, and outputting risk assessment results based on the classification prediction model to perform the risk assessment for the aflatoxin contamination of the sample, which includes: detecting the aflatoxin content of the sample, and subjecting a sample in which aflatoxin is not detected or the aflatoxin content does not exceed the standard to an accelerated microbial metabolism culture experiment, wherein *Aspergillus* will grow in a suspected contaminated sample, quenching the suspected sample by liquid nitrogen and grinding for later use, and detecting the aflatoxin content of the sample, wherein the sample with the aflatoxin content higher than a national limit is directly identified as a high-risk sample, which is the suspected sample.

5. The method according to claim 1, wherein the sample is an agricultural product or food.

6. The method according to claim 1, wherein extracting the warning molecules for the toxigenic strain of *Aspergillus flavus* comprises: performing first extraction by using a solution with a volume ratio of methanol to acetonitrile to water being (2-4):(2-4):(0-1), and then performing second extraction by using a solution with a volume ratio of methanol to dichloromethane to ethyl acetate being (1-3):(1-2):(1-2) to extract the warning molecules for the toxigenic strain of *Aspergillus flavus*, and then centrifugating at a high speed to obtain the sample extract.

7. The method according to claim 1, wherein during analysis by the liquid chromatography-high resolution mass spectrometer, a chromatographic column is a $C_{18}$ reverse chromatographic column, and a mass spectrometry analysis acquisition mode is divided into a positive ion mode and a negative ion mode run which are operated separately; the acquisition mode is a data-dependent acquisition mode, and the primary mass spectrometry data and secondary fragment ion data are acquired simultaneously to perform qualitative and quantitative analysis, thereby obtaining the analysis results of the warning molecules.

8. The method according to claim 1, wherein the detection and analysis by the liquid chromatography-high resolution mass spectrometer contains an internal standard substance, and the internal standard is camphoric acid (a negative ion mode) and 2-chlorophenylalanine (a positive ion mode).

9. The method according to claim 1, wherein the main secondary mass spectrometry ion peaks of the warning molecule 5-methoxysterigmatocystin (5-MST) comprise 350.0809 Da, 340.0571 Da, 322.04675 Da, 311.05469 Da and 285.0098 Da;
   the secondary mass spectrometry ion peaks of the warning molecule versiconol (VOH) comprise: 329.06546 Da, 341.09506 Da, and 359.07596 Da; and
   the main secondary mass spectrometry ion peaks of the warning molecule versicolorin B (Ver B) comprise: 311.0542 Da, 311.0187 Da, and 283.0238 Da.

* * * * *